US009513222B2

(12) United States Patent
Lenhert et al.

(10) Patent No.: US 9,513,222 B2
(45) Date of Patent: *Dec. 6, 2016

(54) SCALABLE LIPOSOME MICROARRAY SCREENING

(71) Applicant: FLORIDA STATE UNIVERSITY RESEARCH FOUNDATION, Tallahassee, FL (US)

(72) Inventors: Steven Lenhert, Tallahassee, FL (US); Troy W. Lowry, Tallahassee, FL (US); Aubrey Kusi-Appiah, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/413,319

(22) PCT Filed: Jul. 12, 2013

(86) PCT No.: PCT/IB2013/055762
§ 371 (c)(1),
(2) Date: Jan. 7, 2015

(87) PCT Pub. No.: WO2014/009929
PCT Pub. Date: Jan. 16, 2014

(65) Prior Publication Data
US 2015/0168301 A1 Jun. 18, 2015

Related U.S. Application Data

(60) Provisional application No. 61/671,214, filed on Jul. 13, 2012.

(51) Int. Cl.
G01N 21/64 (2006.01)
B05D 3/12 (2006.01)
B01L 3/02 (2006.01)
B01L 3/00 (2006.01)

(52) U.S. Cl.
CPC ......... G01N 21/6456 (2013.01); B01L 3/0258 (2013.01); B01L 3/5088 (2013.01); B05D 3/12 (2013.01); B01L 2300/161 (2013.01); G01N 2201/061 (2013.01)

(58) Field of Classification Search
CPC ............ G01N 21/6456; B01L 3/0258; B01L 3/5088; B05D 3/12
USPC ....................................................... 506/14
See application file for complete search history.

(56) References Cited

U.S. PATENT DOCUMENTS

| 6,548,263 B1 | 4/2003 | Kapue et al. |
| 7,531,366 B2 | 5/2009 | Abbott et al. |
| 2002/0086340 A1* | 7/2002 | Veerapandian .... G01N 15/1404 435/7.23 |
| 2007/0004046 A1 | 1/2007 | Abbott et al. |
| 2007/0059765 A1 | 3/2007 | Wang et al. |
| 2007/0178534 A1 | 8/2007 | Murphy et al. |
| 2009/0181172 A1 | 7/2009 | Parpia et al. |
| 2009/0238853 A1* | 9/2009 | Liu ..................... A61L 27/3633 424/423 |
| 2010/0009344 A1 | 1/2010 | Israel et al. |
| 2010/0124626 A1* | 5/2010 | Vossler .................... B41C 3/06 428/40.1 |
| 2010/0221815 A1 | 9/2010 | Abbott et al. |
| 2012/0070885 A1 | 3/2012 | Lenhert |
| 2012/0075441 A1 | 3/2012 | Lenhert |
| 2012/0098974 A1 | 4/2012 | Lenhert et al. |
| 2012/0231489 A1 | 9/2012 | Lenhert |
| 2012/0258292 A1 | 10/2012 | Lenhert et al. |
| 2013/0137599 A1 | 5/2013 | Lenhert et al. |
| 2014/0051602 A1 | 2/2014 | Lenhert |

FOREIGN PATENT DOCUMENTS

| WO | 2005015792 | 2/2005 |
| WO | 2006078952 | 7/2006 |
| WO | 2011017487 | 2/2011 |
| WO | 2014013456 | 1/2014 |

OTHER PUBLICATIONS

Yamazaki et al., BMC Biotechnology, 2005, 5, 18, pp. 1-11.*
International Preliminary Report on Patentability received in PCT Application No. PCT/IB2013/055762 mailed Jan. 22, 2015.
Barenholz, Y., Gibbes, D., Litman, B. J., Goll, J., Thompson, T. E., and Carlson, F. D., "A simple method for the preparation of homogeneous phospholipid vesicles," Biochemistry 16, 2806-10 (1977).
Gustafsson, J., Arvidson, G., Karlsson, G., and Almgren, M. "Complexes between cationic liposomes and DNA visualized by Cryo-Tem," BBA-Biomembranes 1235, 305-12 (1995).
Kwon, C. H., Wheeldon, I., Kachouie, N. N., Lee, S. H., Bae, H., Sant, S., Fukuda, J., Kang, J. W., Khademhosseini, A., "Drug-eluting microarrays for cell-based screening of chemical-induced apoptosis," Anal. Chem. 83, 4118-25 (2011).

(Continued)

Primary Examiner — Larry Riggs
Assistant Examiner — Karla Dines
(74) Attorney, Agent, or Firm — Fox Rothschild LLP

(57) ABSTRACT

A method comprising the following steps: (a) contacting a topographically structured stamp to an array of spots comprising lipid ink on a palette to force the lipid ink of each of the spots into recesses of the topographically structured stamp, (b) removing the palette from the topographically structured stamp so that at least some the lipid ink from each of the spots is retained in the recesses of the topographically structured stamp, and (c) printing the lipid ink in each of the recesses on a substrate as an array of stamped spots using the topographically structured stamp to thereby form a patterned substrate, wherein the recesses have one or more recess patterns, wherein each stamped spot of the array of stamped spots comprises lipid multilayer structure, and wherein the patterned array is based on the one or more recess patterns.

18 Claims, 33 Drawing Sheets

(56) References Cited

OTHER PUBLICATIONS

Malam, Y., Loizidou, M., and Seifalian, A. M., "Liposomes and nanoparticles: nanosized vehicles for drug delivery in cancer," Trends Pharmacol. Sci. 30, 592-99 (2009).
Porter, C. J. H., Trevaskis, N. L., and Charman, W. N., "Lipids and lipid-based formulations:optimizing the oral delivery of lipophilic drugs," Nat. Rev. Drug Discov. 6, 231-48 (2007).
Torchilin, V. P., "Micellar nanocarriers: pharmaceutical perspectives," Pharm. Res. 24, 1-16 (2007).
Koren, E., and Torchilin, V. P., "Drug carriers for vascular drug delivery," IUBMB Life 63, 586-95 (2011).
Gregoriadis, G., "Engineering liposomes for drug delivery: progress and problems," Trends in Biotechnology 13, 527-37 (1995).
Kusi-Appiah, A. E., Vafai, N., Cranfill, P. J., Davidson, M. W., and Lenhert, S., "Lipid multilayer microarrays for in vitro lipomosomal drug delivery and screening," Biomaterials 33, 4187-94 (2012).
Majd, S, and Mayer, M., "Hydrogel stamping of arrays of supported lipid bilayers with various lipid compositions for the screening of drug-membrane and protein-membrane interactions," Angew. Chem. Int. Ed. 44, 6697-6700 (2005).
Yamazaki, V., Sirenko, O., Schafer, R. J., Nguyen, L., Gutsmann, T., Brade, L., and Groves, J. T., "Cell membrane array fabrication and assay technology," BMC Biotechnology 2005, doi:10.1186/1472-6750-5-18 (2005).
Lenhert, S., Brinkmann, F., Laue, T., Walheim, S., Vannahme, C., Klinkhammer, S., Xu, M., Sekula, S., Mappes, T., Schimmel, T., and Fuchs, H., "Lipid multilayer gratings," Nat. Nanotechnol. 5, 275-79 (2010).
Lenhert, S., Sun, P., Wang, Y. H., Fuchs, H., and Mirkin, C. A., "Massively parallel dip-pen nanolithography of heterogeneous supported phospholipid multilayer patterns," Small 3, 71-75 (2007).
Sekula, S., Fuchs, J., Weg-Remers, S., Nagel, P., Schuppler, S., Fragala, J., Theilacker, N., Franzreb, M., Wingren, C., Ellmark, P., Borrebaeck, C. A. K., Mirkin, C. A., Fuchs, H., and Lenhert, S., "Multiplexed lipid dip-pen nanolithography on subcellular scales for the templating of functional proteins and cell culture," Small 4, 1785-93 (2008).
Nafday, O. A., and Lenhert, S. "High-throughput optical quality control of lipid multilayers fabricated by dip-pen nanolithography," Nanotechnology 22, doi:225301 (2011).
Perino-Gallice, L., Fragneto, G., Mennicker, U., Salditt, T., and Rieutord, F., "Dewetting of solid-supported multilamellar lipid layers," Eur. Phys. J. E 8, 275-82 (2002).
Mathieu, M. Schunk, D., Franzka, S., Mayer, C., and Hartmann, N., "Temporal stability of photothermally fabricated micropatterns in supported phospholipid multilayers," J. Vac. Sci. Technol. A 28, 953-57 (2010).
Perl, A., Reinhoudt, D. N., and Huskens, J., "Microcontact printing: limitations and achievements," Adv. Mater. 21, 2257-68 (2009).
Nafday, O. A., Lowry, T. W., and Lenhert, S., "Multifunctional lipid multilayer stamping," Small 8, 1021-28 (2012).
Braunschweig, A. B., Huo, F. W., and Mirkin, C. A., "Molecular printing," Nat. Chem. 1, 353-58 (2009).
Salaita, K., Wang, Y. H., and Mirkin, C. A., "Applications of dip-pen nanolithography," Nat. Nanotechnol. 2, 145-55 (2007).
Ginger, D. S., Zhang, H., and Mirkin, C. A., "The evolution of dip-pen nanolithography," Angew. Chem. Int. Ed. 43, 30-45 (2004).
Zhang, M., Bullen, D., Chung, S. W., Hong, S., Ryu, K. S., Fanm Z. F., and Mirkin, C. A., and Liu, C., "A MEMS nanoplotter with high density parallel dip-pen nanolithography probe arrays," Nanotechnology 13, 212-17 (2002).
Xia, Y. N., and Whitesides, G. M., "Soft lithography," Annu. Rev. Mater. Sci. 28, 153-84 (1998).
Huo, F., Zheng, Z., Zheng, G, Giam, L., Zhang, H., and Mirkin, C. A., "Polymer pen lithography," Science 321 1658-60 (2008).
Chou, S. Y., Krauss, P. R., and Renstrom, P. J., "Imprint lithography with 25-nanometer resolution," Science 272, 85-87 (1996).
Lenhert, S., Mirkin C. A., and Fuchs, H., "In situ lipid dip-pen nanolithography under water," Scanning 32, 15-23 (2010).

Mendez-Vilas, A., Jodar-Reyes, A. B., and Gonzalez-Martin, M. L., "Ultrasmall liquid droplets on solid surfaces: production, imaging, and relevance for current wetting research," Small 5, 1366-90 (2009).
Barbulovic-Nad, et al., "Bio-microarray fabrication techniques—a review", Critical Reviews in Biotechnology, vol. 26. No. 4, pp. 237-259, (2006).
Renalt, et al., "Fabricating Microarrays of Functional Protein Using Affinity Contact Printing," Angewandte Chemie, vol. 114, Issue 13, pp. 2426-2429, (2002).
Szokam F., and Paphadjopoulos, D., "Comparative Properties and Methods of Preparation of Lipid Vesicles (liposomes)," Annu. Rev. Biophys. Bio 9, 467-508 (1980).
Moran-Mirabal, J. M., Edel, J. B., Meyer, G. D., Throckmorton, D., Singh, A. K., and Craighead, H. G., "Micrometer-sized supported lipid bilayer arrays for bacterial toxin binding studies through total internal reflection fluorescence microscopy," Biophys. J. 89, 296-305 (2005).
Deng, Y., Wang, Y., Holtz, B. Li, J., Traaseth, N., Veglia, G., Stottrup, B. J., Elde, R., Pei, D., Guo, A., and Zhu, X. Y., "Fluidic and air-stavle supported lipid bilayer and cell-mimicking microarrays," J. Am. Chem. Soc. 130, 6267-71 (2008).
Howbrook, D. N., van der Valk, A. M., O'Shaughnessy, M. C., Sarker, D. K., Baker, S. C., and Lloyd, A. W., "Developments in microarray technologies," Drug Discov. Today 15, 648-51 (2003).
Eteshola, E., and Leckband, D., "Development and characterization of an ELISA assay in PDMS microfluidic channels," Sens. Actuator B-Chem. 72, 129-33 (2001).
Piner, R. D., Zhu, J., Xu, F., Hong, S. H., and Mirkin, C. A., "Dip-pen" nanolithography, Science 283, 661-63.
Salaita, K., Wang, Y. H., Fragala, J., Vega, R. A., Liu, C., Mirkin, C. A. "Massively parallel dip-pen nanolithography with 55000-pen two-dimensional arrays," Angew. Chem. Int. Ed. 45, 7220-23 (2006).
Kusi-Appiah, A., Vafai, N., Cranfill, P. J., Davidson, M. W. & Lenhert, S., "Lipid multilayer microarrays for in vitro liposomal drug delivery and screening," Biomaterials 33(16) 4187-94 (2012).
Jang, J. W., Smetana, A., and Stiles, P., "Multi-ink pattern generation by dip-pen nanolithography," Scanning 32, 24-29 (2010).
Torchilin, V. P., "Recent advances with liposomes as pharmaceutical carriers," Nat. Rev. Drug Discov. 4, 145-60 (2005).
Szymanski, P., Markowicz, M. & Mikiciuk-Olasik, E. Adaptation of High-Throughput Screening in Drug Discovery—Toxicological Screening Tests. International Journal of Molecular Sciences 13, 427-452 (2012).
International Search Report & Written Opinion mailed Mar. 5, 2014 in corresponding PCT/IB2013/055762.
Marty et al., Structural Analysis of DNA Complexation With Cationic Lipids, Nucleic Acids Research, 2009, 37(3), 849-857.
Sanjana et al., A Fast Flexible Ink-Jet Printing Method for Patterning Dissociated Neurons in Culture, Journal of Neuroscience Methods, 2004, 136, 151-163.
van Horssen, R. and ten Hagen, T. L. M., "Crossing barriers: The new dimension of 2D cell migration assays," Journal of Celular Physiology., 226, 288-290 (2011).
Sampieri, K. and Fodde, R., "Cancer stem cells and metastasis," Seminars in Cancer Biology., 22, 187-193 (2012).
Brabletz, T., Jung, A., Spaderna, S., Hlubek F., and Kirchner, T., "Opinion: migrating cancer stem cells—an integrated aoncept of malignant tumour progression." Nature Reviews Cancer, 5, 744-749 (2005).
Eilken, H. M. and Adams, R. H., "Dynamics of endothelial cell behavior in sprouting angiogenesis," Current Opinion in Sell Biology, 22, 617-625 (2010).
Griffioen, A. W. and Molema, G., "Anti-angiogenesis: making the tumor vulnerable to the immune system," Pharmacoogy Review., 52, 237-268 (2000).
Aman, A. and Piotrowski, T. "Cell migration during morphogenesis," Developmental Biology, 341, 20-33 (2010).
Weijer, C. J. "Collective cell migration in development," Journal of Cell Science., 122, 3215-3223 (2009).

(56) References Cited

OTHER PUBLICATIONS

Liang, C. C., Park, A. Y. and Guan, J. L., "In vitro scratch assay: a convenient and inexpensive method for analysis of cell imgration invitro," Nature Protocols., 2, 329-333 (2007).
Valster, A., Tran, N. L., Nakada, M., Berens, M. E., Chan A. Y. and Symons, M., "Cell migration and invasion assays" Methods, 37, 208-215 (2005).
Lenhert, S., Meier, M. B., Meyer, U., Chi, L. F. and Wiesmann, H. P., "Osteoblast alignment, elongation and migration on grooved polystyrene surfaces patterned by Langmuir-Blodgett lithography," Biomaterials, 26, 563-570 (2005).
Shin, K. D., Lee, M. Y., Shin, D. S., Lee, S., Son, K. H., Koh, S. Paik, Y. K., Kwon B. M. and Han, D. C., "Blocking umor cell migration and invasion with biphenyl isoxazole derivative KRIBB3, a synthetic molecule that inhibits Hsp27 3hosphorylation," Journal of Biological Chemistry., 280, 41439-41448 (2005).
Gough, W., Hulkower, K. I., Lynch, R., McGlynn, P., Uhlik, M., Yan, L. and Lee, J. A, "A quantitative, facile, and highhroughput image-based cell migration method is a robust alternative to the scratch assay," Journal of Biomolecular Screening, 16, 155-163 (2011).
Attoub, S., Hassan, A. H., Vanhoecke, B., Iratni, R., Takahashi, T. Gaben, A.-M., Bracke, M., Awad, S., John, A., Kamalboor, H. A., Al Sultan, M. A. Arafat, K. Gespach, C. and Petroianu, G., "Inhibition of cell survival, invasion, tumor growth and histone deactylase activity by the dietary flavonoid luteolin in human epitholioid cancer cells," European Journal of Pharmacology, 651, 18-25 (2011).
Chung, S., Sudo, R., Mack, P. J., Wan, C. R., Vickerman, V. and Kamm, R. D., "Cell migration into scaffolds under comilture conditions in a microfluidic platform," Lab on a Chip, 9, 269-275 (2009).
Conant, C. G., Nevill, J. T., Schwartz, M. and Ionescu-Zanetti, C., "Wound healing assays in well-plate coupled microfluidic devices with controlled parallel flow," Journal of the Association for Laboratory Automation, 15, 52-57 2010).
Huang, X. W., Li, L., Tu, Q., Wang, J. C., Liu, W. M., Wang, X. Q., Ren, L. and Wang, J. Y., "On-chip cell migration assay for quantifying the effect of ethanol on MCF7 human breast cancer cells," Microfluid Nanofluid, 10, 1333-1341 :2011).
Poujade, M., Grasland-Mongrain, E., Hertzog, A , Jouanneau, J., Chavrier, P., Ladoux, B., Buguin, A. and Silberzan, J. "Collective migration of an epithelial monolayer in response to a model wound," Proceedings of the National Academy of Sciences of the United States of America, 104, 15988-15993 (2007).
Wang, L., Zhu, J., Deng, C., Xing, W. L. and Cheng, J., "An automatic and quantitative on-chip cell migration assay using self-assembled monolayers combined with real-time cellular impedance sensing," Lab on a Chip, 8, 872-878 (2008).
Kim, B. J. and Wu, M. M., "Microfluidics for mammalian cell chemotaxis," Annals of Biomedical Engineering, 40, 1316-1327 (2012).
Liu, T. J., Lin, B. C. and Qin, J. H., "Carcinoma-associated fibroblasts promoted tumor spheroid invasion on a microcrofluidic 3D co-culture device," Lab on a Chip, 10, 1671-1677 (2010).
Wang, Z., Kim, M.-C., Marquez, M. and Thorsen, T., "High-density microfludic arrays for cell cytotoxicvity analysis," Lab on a Chip, 7, 740-745 (2007).
Kwak, Y. H., Hong, S. M. and Park, S. S., "A single cell tracking system in real-time," Cellular Immunology, 265, 44-49; 2010).
Puliafito, A., Hufnagel, L., Neveu, P., Streichan, S., Sigal, A., Fygenson, D. K. and Shraiman, B. I. "Collective and single cell behavior in epithelial contact inhibition," Proceedings of the National Academy Sciences of the United States of America, 109, 739-744 (2012).

Adanja, I., Megalizzi, V., Debeir, 0., and Decaestecker, C. "A new method to address unmet needs for extracting individual cell migration features from a large number of cells embedded in 3D volumes," PLoS One, 6 (2011).
Diaz-Mochon, J. J., Tourniaire, G. and Bradley, M., "Microarray platforms for enzymatic and cell-based assays," Shemical Society Reviews, 36, 449-457 (2007).
Yarrow, J. C Totsukawa, G., Charras, G. T. and Mitchison, T. J. "Screening for cell migration inhibitors via automated microscopy reveals a Rho-kinase inhibitor," Chemistry & Biology, 12, 385-395 (2005).
Tourniaire, G. , Collins, J., Campbell, S., Mizomoto, H. Ogawa, S., Thaburet, J. F. and Bradley, M. "Polymer microarrays for cellular adhesion," Chemical Communications, 2118-2120 (2006).
Balakin, K. V., Savchuk, N. P. and Tetko, I. V., "In silico approaches of aqueous and DMSO solubility of drug-like compounds: trends, problems and solutions," Current Medicinal Chemistry, 13, 223-241 (2006).
Moran-Mirabal, et al., "Micrometer-sized supported lipid bilayer arrays for bacterial toxin binding studies through total internal reflection fluorescence microscopy," Biophys. J. 89, 296-305 (2005).
Heller, M.J., "DNA microarray technology: devices, systems, and applications," Annu. Rev. Blamed, Eng. 4 129-53 (2002).
Majd, S. and Mayer, M., "Generating arrays with high content and minimal consumption of functional membrane proteins," Journal of American Chemical Society, 130, 16060-16064 (2008).
Diguet, A. Le Berre, M. Chen, Y. and Baigl, D., "Preparation of phospholipid multilayer patterns of controlled size and thickness by capillary assumbly on a microstructured substrate," Small, 5, 1661-1666 (2009).
Brinker, C. J., Lu, Y. F., Sellinger, A. and Fan, H. Y., "Evaporation-induced self-assembly: Nanostructures made easy," Advanced Materials, 11, 579-+(1999).
Yuan, B., Xing, L. L., Zhang, Y. D., Lu, Y., Mai, Z. H. and Li, M., "Self-assembly of highly oriented lamellar nanoparticle-phospholipid nanocomposites on solid surfaces," Journal of American Chemical Society, 129, 11332-+(2007).
Groves, J. T., Mahal, L. K. and Bertozzi, C. R. Langmuir, "Control of cell adhesion and growth with micropatterned supported lipid membranes," 17, 5129-5133 (2001).
Tang, F. and Hughes, J. A., "Synthesis of a single-tailed cationic lipid and investigation of its transfection," Journal of Controlled Release, 62, 345-358 (1999).
Fayad, W., Rickardson, L., Haglund, C., Olofsson, M. H., D'Arcy, P., Larsson, R., Linder, S. and Fryknas, M., Identification of agents that induce apoptosis oif multicellular tumour spheroids: enrichment for mitotic inhibitors with hydrophobic properties, Chemical Biology and Drug Design, 78, 547-557 (2011).
J-W. Zhu, H. H Nagasawa, F. Nagura, S. B. Mohamad, Y. Uto, K. Ohkura and H. Hari, "Elucidation of Strict Structural Requirements of Brefeldin A as an Inducer of Differentiations and Apoptosis," Bioorg. Med. Chem., 8, 455-463 (2000).
Harris, D.J., et al., "Marangoni Effects on Evaporative Lithographic Patterning of Colloidal Films," vol. 15, Issue 24(8), 4 pages, Langmuir 2008.
Witte, M. B. and Barbul, A., "General principles of wound healing," The Surgical Clinics of North America., 77, 509-+(1997).
Bailey, S. N., Sabatini D. M. and Stockwell, B. R., "Microarrays of small molecules embedded in biodegradable polymers for use in mammalian cell-based screens," Proceedings of the National Academy Sciences of the United States of America, 101, 16144-16149 (2004).
Jacob, S. W. and Herschler, R. "Pharmacology of DMSO," Cryobiology, 23, 14-27 (1986).
Grein, T. A., Freimark, D., Weber, C., Nude!, K., Wallrapp, C. and Czermak, P., "Alternatives to dimethylsulfoxide for serum-free cryopreservation of human mesenchymal stem cells," International Journal of Artificial Organs, 2010, 33, 370-380.

\* cited by examiner

SCALABLE LIPOSOME MICROARRAY SCREENING

CROSS-REFERENCE TO RELATED APPLICATIONS

This application claims benefit of priority to U.S. Provisional Patent Application No. 61/671,214, entitled "SCALABLE LIPOSOME MICROARRAY SCREENING" filed Jul. 13, 2012, which is incorporated herein by reference in its entirety.

This application makes reference to the above-cited references and the following U.S. patent applications: U.S. Provisional Patent Application No. 61/383,775, entitled "HIGH THROUGHPUT OPTICAL QUALITY CONTROL OF PHOSPHOLIPID MULTILAYER FABRICATION VIA DIP PEN NANOLITHOGRAPHY (DPN)," filed Sep. 17, 2010. U.S. Provisional Patent Application No. 61/387,764, entitled "NOVEL DEVICE FOR DETECTING AND ANALYZING AQUEOUS SAMPLES," filed Sep. 21, 2010. U.S. Provisional Patent Application No. 61/387,550, entitled "LIPID MULTILAYER GRATINGS," filed Sep. 29, 2010. U.S. Provisional Patent Application No. 61/387,556, entitled "LIPID MULTILAYER GRATINGS FOR SEMI-SYNTHETIC QUORUM SENSORS," filed Sep. 29, 2010. U.S. Provisional Patent Application No. 61/451,619, entitled "IRIDESCENT SURFACES AND APPARATUS FOR REAL TIME MEASUREMENT OF LIQUID AND CELLULAR ADHESION," filed Mar. 11, 2011. U.S. Provisional Patent Application No. 61/451,635, entitled "METHODS AND APPARATUS FOR LIPID MULTILAYER PATTERNING," filed Mar. 11, 2011. U.S. Provisional Patent Application No. 61/501,298, entitled "LIPOSOME MICROARRAY SURFACE AND THEIR USE FOR CELL CULTURE SCREENING," filed Jun. 27, 2011. U.S. patent application Ser. No. 13/234,540, entitled "OPTICAL METHOD FOR MEASURING HEIGHT OF FLUORESCENT PHOSPHOLIPID FEATURES FABRICATED VIA DIP-PEN NANOLITHOGRAPHY," filed Sep. 11, 2011. U.S. patent application Ser. No. 13/238,498, entitled "INTEGRATED DEVICE FOR ANALYZING AQUEOUS SAMPLES USING LIPID MULTILAYER," filed Sep. 21, 2011. U.S. patent application Ser. No. 13/248,250, entitled "SEMI-SYNTHETIC QUORUM SENSORS," filed Sep. 29, 2011. U.S. Provisional Patent Application No. 61/570,490, entitled "LIPID MULTILAYER MICROARRAYS FOR IN VITRO LIPOSOMAL DRUG DELIVERY AND SCREENING," filed Dec. 14, 2011. U.S. Provisional Patent Application No. 61/577,834, entitled "HIGH THROUGHPUT SCREENING METHOD AND APPARATUS," filed Dec. 20, 2011. U.S. Provisional Patent Application No. 61/577,910, entitled "NANOSTRUCTURED LIPID MULTILAYER FABRICATION AND DEVICES THEREOF," filed Dec. 20, 2011. U.S. patent application Ser. No. 13/417,650, entitled "IRIDESCENT SURFACES AND APPARATUS FOR REAL TIME MEASUREMENT OF LIQUID AND CELLULAR ADHESION," filed Mar. 12, 2012. U.S. patent application Ser. No. 13/417,588, entitled "METHODS AND APPARATUS FOR LIPID MULTILAYER PATTERNING," filed Mar. 12, 2012. U.S. patent application Ser. No. 13/534,772, entitled "LIPID MULTILAYER MICROARRAYS AND THEIR USE FOR CELL CULTURE SCREENING," filed Jun. 27, 2012. U.S. Provisional Patent Application No. 61/672,505, entitled "SURFACE SUPPORTED LIPOSOME NANOARRAYS AS BIOMIMETIC SENSORS," filed Jul. 17, 2012. U.S. Provisional Patent Application No. 61/841,980, entitled "EVAPORATIVE EDGE LITHOGRAPHY (EEL) OF A LIPOSOMAL DRUG MICROARRAY FOR CELL MIGRATION ASSAYS," filed Jul. 2, 2013. The entire disclosure and contents of these patent applications are incorporated herein by reference.

BACKGROUND

Field of the Invention

The present invention relates to scalable liposome microarray screening.

Related Art

Most microarrays take the approach of covalently linking the molecule to be screened to the surface, or confining the molecules of interest to a two-dimensional lipid bilayer. The liposome microarray technology described here provides a small, yet three-dimensional volume in which encapsulated molecules are dispersed. For drug screening applications, this allows the delivery of candidate molecules to the cell for internalization at concentrations relevant to clinical dosages.

SUMMARY

According to a first broad aspect, the present invention provides a method comprising the following steps: (a) contacting a topographically structured stamp to an array of spots comprising lipid ink on a palette to force the lipid ink of each of the spots into recesses of the topographically structured stamp, (b) removing the palette from the topographically structured stamp so that at least some the lipid ink from each of the spots is retained in the recesses of the topographically structured stamp, and (c) printing the lipid ink in each of the recesses on a substrate as an array of stamped spots using the topographically structured stamp to thereby form a patterned substrate, wherein the recesses have one or more recess patterns, wherein each stamped spot of the array of stamped spots comprises lipid multilayer structure, and wherein the patterned array is based on the one or more recess patterns.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE PREFERRED EMBODIMENTS

Definitions

Figure 1:
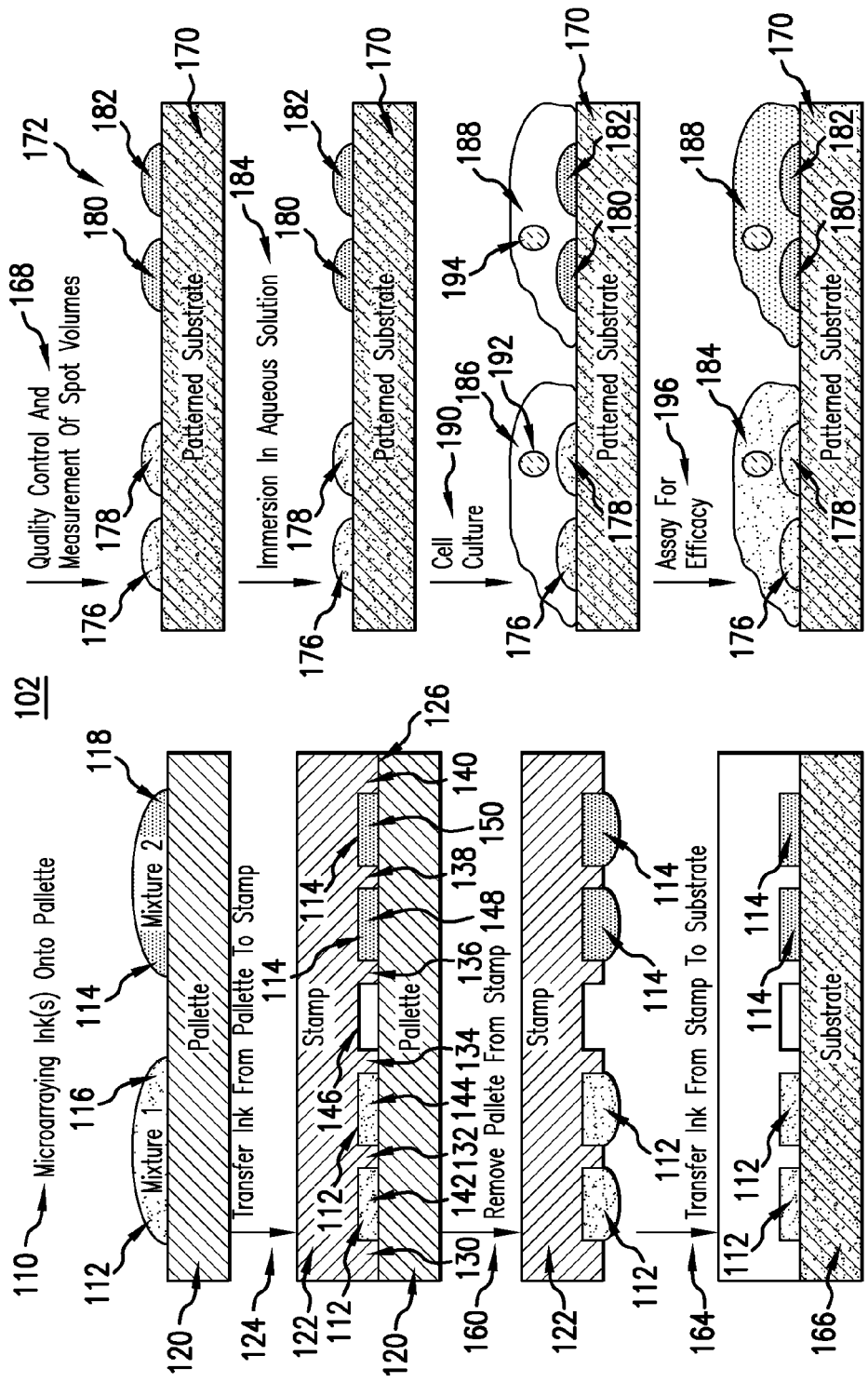
FIG. 1 is a schematic illustration showing the lipid multilayer stamping process used in this present invention.

Where the definition of terms departs from the commonly used meaning of the term, applicant intends to utilize the definitions provided below, unless specifically indicated.

For purposes of the present invention, it should be noted that the singular forms, "a," "an" and "the" include reference to the plural unless the context as herein presented clearly indicates otherwise.

For purposes of the present invention, directional terms such as "top," "bottom," "upper," "lower," "above," "below," "left," "right," "horizontal," "vertical," "up," "down," etc., are used merely for convenience in describing the various embodiments of the present invention. The embodiments of the present invention may be oriented in various ways. For example, the diagrams, apparatuses, etc., shown in the drawing figures may be flipped over, rotated by 90° in any direction, reversed, etc.

For purposes of the present invention, a value or property is "based" on a particular value, property, the satisfaction of a condition, or other factor, if that value is derived by performing a mathematical calculation or logical decision using that value, property or other factor.

For purposes of the present invention, the term "analyte" refers to the conventional meaning of the term "analyte," i.e., a substance or chemical constituent of a sample that is being detected or measured in a sample. In one embodiment of the present invention, a sample to be analyzed may be an aqueous sample, but other types of samples may also be analyzed using a device of the present invention.

For purposes of the present invention, the term "array" refers to a one-dimensional or two-dimensional set of microstructures. An array may be any shape. For example, an array may be a series of microstructures arranged in a line, such as an array of squares. An array may be arranged in a square or rectangular grid. There may be sections of the array that are separated from other sections of the array by spaces. An array may have other shapes. For example, an array may be a series of microstructures arranged in a series of concentric circles, in a series of concentric squares, a series of concentric triangles, a series of curves, etc. The spacing between sections of an array or between microstructures in any array may be regular or may be different between particular sections or between particular pairs of microstructures. The microstructure arrays of the present invention may be composed of microstructures having zero-dimensional, one-dimensional or two-dimensional shapes. The microstructures having two-dimensional shapes may have shapes such as squares, rectangles, circles, parallelograms, pentagons, hexagons, irregular shapes, etc.

For purposes of the present invention, the term "away" refers to increasing the distance between two aligned objects. For example, a contact controlling positioning device may be used to move: a stamp away from an ink palette, an ink palette away from a stamp, a stamp away from a substrate, a substrate away from a stamp, etc.

For purposes of the present invention, the term "biomolecule" refers to the conventional meaning of the term biomolecule, i.e., a molecule produced by or found in living cells, e.g., a protein, a carbohydrate, a lipid, a phospholipid, a nucleic acid, etc.

For purposes of the present invention, the term "camera" refers to any type of camera or other device that senses light intensity. Examples of cameras include digital cameras, scanners, charged-coupled devices, CMOS sensors, photomultiplier tubes, analog cameras such as film cameras, etc. A camera may include additional lenses and filters such as the lenses of a microscope apparatus that may be adjusted when the camera is calibrated.

For purposes of the present invention, the term "contacting surface" refers to a surface of a stamp that contacts a surface onto which a pattern comprising lipid ink is to be printed.

For purposes of the present invention, the term "detector" refers to any type of device that detects or measures light. A camera is a type of detector.

For purposes of the present invention, the term "dot" refers to a microstructure that has a zero-dimensional shape.

For purposes of the present invention, the term "drug" refers to a material that may have a biological effect on a cell, including but not limited to small organic molecules, inorganic compounds, polymers such as nucleic acids, peptides, saccharides, or other biologic materials, nanoparticles, etc.

For purposes of the present invention, the term "encapsulated" refers to being confined by a lipid multilayer or partitioned within a lipid multilayer structure.

For purposes of the present invention, the term "fluorescence" refers to the conventional meaning of the term fluorescence, i.e., the emission of light by a substance that has absorbed light or other electromagnetic radiation of a different wavelength.

For purposes of the present invention, the term "fluorescent" refers to any material or mixture of materials that exhibits fluorescence.

For purposes of the present invention, the term "fluorescent dye" refers to any substance or additive that is fluorescent or imparts fluorescence to another material. A fluorescent dye may be organic, inorganic, etc.

For purposes of the present invention, the term "fluorescent microstructure" refers to a microstructure that is fluorescent. A fluorescent microstructure may be made of a naturally fluorescent material or may be made of a nonfluorescent material, such as a phospholipid, doped with a fluorescent dye.

For purposes of the present invention, the term "fluorescent nanostructure" refers to a nanostructure that is fluorescent. A fluorescent nanostructure may be made of a naturally fluorescent material or may be made of a nonfluorescent material, such as a phospholipid, doped with a fluorescent dye.

For purposes of the present invention, the term "fluid" refers to a liquid or a gas.

For purposes of the present invention, the term "freezing by dehydration" refers to removal of residual water content, for instance by incubation in an atmosphere with low water content, for instance a vacuum (<50 mbar) or at relative humidity below 40% (at standard temperature and pressure).

For purposes of the present invention, the term "grating" refers to an array of dots, lines, or a 2D shape that are regularly spaced at a distance that causes coherent scattering of incident light.

For purposes of the present invention, the term "groove" refers to an elongated recess in a stamp. A groove is not limited to a linear groove, unless clearly specified otherwise in the description below. The dimensions of a groove may change depending on the depth of the groove. For example, a groove may be wider at the top of the groove than at the bottom of the groove, such as in a V-shaped groove.

For purposes of the present invention, the term "groove pattern" refers to the pattern made by one or more grooves of a stamp.

For purposes of the present invention, the term "height" refers to the maximum thickness of the microstructure on a substrate, i.e., the maximum distance the microstructure projects above the substrate on which it is located.

For purposes of the present invention, the term "iridescent" refers to any structure that scatters light.

For purposes of the present invention, the term "iridescent microstructure" refers to a microstructure that is iridescent.

For purposes of the present invention, the term "iridescent nanostructure" refers to a nanostructure that is iridescent.

For purposes of the present invention, the term "irregular pattern" refers to a pattern of ridges and recesses that are not organized in a specific geometric pattern. For example, ridges and or recesses printed to resemble a picture of a human face, a picture of a leaf, a picture of an ocean wave, etc. are examples of irregular patterns. Using photolithography, almost any type of pattern for recesses and/or ridges may be formed in a stamp of the present invention.

For purposes of the present invention, the term "light," unless specified otherwise, refers to any type of electromagnetic radiation. Although, in the embodiments described below, the light that is incident on the gratings or sensors is visible light, the light that is incident on the gratings or sensors of the present invention may be any type of electromagnetic radiation, including infrared light, ultraviolet light, etc., that may be scattered by a grating or sensor. Although, in the embodiments described below, the light that is scattered from the gratings or sensors and detected by a detector is visible light, the light that is scattered by a grating or sensor of the present invention and detected by a detector of the present invention may be any type of electromagnetic radiation, including infrared light, ultraviolet light, etc. that may be scattered by a grating or sensor.

For purposes of the present invention, the term "light source" refers to a source of incident light that is scattered by a grating or sensor of the present invention. In one embodiment of the present invention, a light source may be part of a device of the present invention. In one embodiment a light source may be light present in the environment of a sensor or grating of the present invention. For example, in one embodiment of the present invention a light source may be part of a device that is separate from the device that includes the sensors and detector of the present invention. A light source may even be the ambient light of a room in which a grating or sensor of the present invention is located. Examples of a light source include a laser, a light-emitting diode (LED), an incandescent light bulb, a compact fluorescent light bulb, a fluorescent light bulb, etc.

For purposes of the present invention, the term "line" refers to a "line" as this term is commonly used in the field of nanolithography to refer to a one-dimensional shape.

For purposes of the present invention, the term "lipid" refers to hydrophobic or amphiphilic molecules, including but not limited to biologically derived lipids such as phospholipids, triacylglycerols, fatty acids, cholesterol, or synthetic lipids such as surfactants, organic solvents, oils, etc.

For purposes of the present invention, the term "lipid ink" refers to any material comprising a lipid applied to a stamp.

For purposes of the present invention, the term "lipid multilayer" refers to a lipid coating that is thicker than one molecule.

For purposes of the present invention, the term "lipid multilayer grating" refers to a grating comprising lipid multilayers.

For purposes of the present invention, the term "lipid multilayer structure" refers to a structure comprising one or more lipid multilayers. A lipid multilayer structure may include a dye such as a fluorescent dye.

For purposes of the present invention, the term "low humidity atmosphere" refers to an atmosphere having a relative humidity of less than 40%.

For purposes of the present invention, the term "lyotropic" refers to the conventional meaning of the term "lyotropic," i.e., a material that forms liquid crystal phases because of the addition of a solvent.

For purposes of the present invention, the term "microfabrication" refers to the design and/or manufacture of microstructures.

For purposes of the present invention, the term "microstructure" refers to a structure having at least one dimension smaller than 1 mm. A nanostructure is one type of microstructure.

For purposes of the present invention, the term "nanofabrication" refers to the design and/or manufacture of nanostructures.

For purposes of the present invention, the term "neat lipid ink" refers to a lipid ink consisting of a single pure lipid ink.

For purposes of the present invention, the term "nanostructure" refers to a structure having at least one dimension on the nanoscale, i.e., a dimension between 0.1 and 100 nm.

For purposes of the present invention, the term "patterned substrate" refers to a substrate having a patterned array of lipid multilayer structures on at least one surface of the substrate.

For purposes of the present invention, the term "palette" refers to a substrate having one or more lipid inks that are made available to be picked up or drawn into the recesses or other topographical or chemical features of a stamp. The one or more lipid inks may be located in recesses, inkwells, etc. in the palette, or deposited onto a flat palette.

For purposes of the present invention, the term "palette spot" refers to a single spot of lipid link on a palette. A palette spot may be any shape.

For purposes of the present invention, the term "plurality" refers to two or more. So an array of microstructures having a "plurality of heights" is an array of microstructures having two or more heights. However, some of the microstructures in an array having a plurality of heights may have the same height.

For purposes of the present invention, the term "recess" refers to a recess of any size or shape in a stamp. A recess may have any cross-sectional shape such as a line, a rectangle, a square, a circle, an oval, etc. The dimensions of a recess may change depending on the depth of the recess. For example, a recess may be wider at the top of the recess than at the bottom of the recess, such as in a V-shaped recess. An example of a recess is a groove.

For purposes of the present invention, the term "recess pattern" refers to the pattern made by one or more recesses of a stamp.

For purposes of the present invention, the term "regular pattern" refers to a pattern of ridges and recesses organized in a specific geometric pattern. For example, a series of parallel recesses and/or lines is one example of a regular pattern. One or more arrays of ridges and recesses arranged in a square, a circle, an oval, a star, etc. is another example of a regular pattern.

For purposes of the present invention, the term "patterned array" refers to an array arranged in a pattern. A patterned array may comprise a single patterned array of lipid multilayer structures or two or more patterned arrays of lipid multilayer structures. Examples of patterned arrays of lipid multilayer structures are a patterned array of dots, a patterned array of lines, a patterned array of squares, etc.

For purposes of the present invention, the term "printing" refers to depositing a material, such as lipid ink, on a substrate.

For purposes of the present invention, the term "removing" refers to removing two objects from each other by moving one or both objects away from each other. For example, a stamp may be removed from a palette or substrate by moving the stamp away from the palette or substrate, by moving the palette or substrate away from the stamp or by moving both the stamp and the palette or substrate away from each other.

For purposes of the present invention, the term "ridge" refers to any raised structure. A ridge is not limited to a linear ridge, unless clearly specified otherwise in the description below. A ridge may have any cross-sectional shape such as a line, a rectangle, a square, a circle, an oval, etc. The dimensions of a ridge may change depending on the depth of a neighboring groove. For example, a ridge may be wider at the bottom of the ridge than at the top of the ridge, such as in a V-shaped ridge. A ridge may constitute the entire contacting surface of a stamp after recesses have been formed, etched, etc. into the stamp.

For purposes of the present invention, the term "scattering" and the term "light scattering" refer to the scattering of light by deflection of one or more light rays from a straight path due to the interaction of light with a grating or sensor. One type of interaction of light with a grating or sensor that results in scattering is diffraction.

For purposes of the present invention, the term "sensor" and the term "sensor element" are used interchangeably, unless specified otherwise, and refer to a material that may be used to sense the presence of an analyte.

For purposes of the present invention, the term "square" refers to a microstructure that is square in shape, i.e., has a two-dimensional shape wherein all sides are equal.

For purposes of the present invention, the term "stamped spot" refers to an area of a patterned surface of lipid nanostructures that originates from a single palette spot on an ink palette used as a source of lipid ink by stamp in depositing the lipid nanostructure. A stamped spot may be any shape.

For purposes of the present invention, the term "topographically structured stamp" refers to a stamp having recesses that form one or more recess patterns. For simplicity, unless specifically indicated otherwise, the term "stamp" refers to a topographically structured stamp.

For purposes of the present invention, the term "toward" refers to decreasing the distance between two aligned objects. For example, a contact controlling positioning device may be used to move: a stamp towards an ink palette, an ink palette towards a stamp, a stamp towards a substrate, a substrate towards a stamp, etc.

Description

Liposomes or vesicles are three-dimensional, self-organized, nanostructured lipid particles that are widely used as drug- and gene-delivery vehicles.[1-7] The use of lipids as delivery vectors for delivery of materials to cells has become a widely studied field due to the potential of utilizing them to deliver both lipophilic and hydrophilic drugs and nutrients through liposomes.[8,9] The efficiency of delivery from solution using cationic phospholipids has been extensively studied making them a prime material for efficient delivery of materials into cells. Liposomes have been found to enhance the efficacy of anticancer drugs. There is evidence that lipid composition affects cellular uptake and the ability for the drug to kill cancer cells.

Lipid multilayer microstructures and nanostructures are a type of nanomaterial that are effectively multilamellar liposomes confined to a surface. This allows analysis and assays developed for lipid bilayers to be applied to multilayered liposome like structures, which are capable of encapsulating materials. One application of these materials is in the fabrication of small molecule microarrays for drug screening, where drugs encapsulated in the lipid multilayer nanostructures can be delivered to cells cultured on these surfaces for screening of drug efficacy in a microarray format.[10]

Microarraying techniques have been very successful in biotechnology for carrying out a large number of experiments on a single surface. Microarrays of different types of lipids have been proposed for molecular screening applications.[11,12] Spotting techniques are typically used to create arrays of lipid bilayers that are composed of different lipid materials on a surface that allows lipid-bilayer formation.[13,14] Methods of fabricating lipid multilayer microarrays include dip-pen nanolithography (DPN),[15,16,17,18] dewetting on a prepatterned surface,[19] and photothermal patterning,[20] microcontact printing,[21] and lipid multilayer stamping.[22] Micro- and nanostructured lipid multilayers on surfaces hold the promise of combining certain properties of solution-based liposomes with surface-based capabilities.

Most microarrays take the approach of covalently linking the molecule to be screened to the surface, or confining the molecules of interest to a two-dimensional lipid bilayer. The liposome microarray technology described here provides a small, yet three-dimensional volume in which encapsulated molecules are dispersed. For drug screening applications, this allows the delivery of candidate molecules to the cell for internalization at concentrations relevant to clinical dosages. Microarray technology, however, has been thoroughly developed for integrating a large number of different multiple materials onto a surface. This approach has been particularly successful for DNA microarrays, where DNA molecules are covalently linked to the surface. Microarray techniques include the use of piezo-based inkjet dispenser systems for depositing molecules like DNA onto substrates and pin based fluid transfer systems. In addition, photolithographic methods have been used for in situ high density DNA microarray fabrication by DNA synthesis on the chip, for instance by companies like Affymetrix® which increase the number of experiments that can be done on these arrays without compromising on the quality of the experiments.[23,24] The use of microfluidics has also seen success in increasing the throughput of biochemical analysis by using aqueous drops dispersed in oil as picoliter reaction vessels to identify new mutants of the enzyme horseradish peroxidase and screening at the rate of ~$10^8$ individual reactions in 10 hours.[25] Microarrays have also been applied to the patterning of antibodies and lipids. Stainless steel pins have been used for printing microarrays of DNA and proteins. Dip-pen nanolithography (DPN) is a method that uses the tip from an AFM to deliver materials to a surface in a direct writing process, and it can fabricate arbitrary structures from a variety of molecular inks.[26-29] The use of masks is not required, and sub-100-nm resolution can be achieved.[29] DPN is also capable of high throughput when carried out with parallel tip arrays.[30,31] Similar approaches to nanosurface and microsurface patterning include soft lithography[32] and polymer pen lithography.[33] Previous work has established the concept of using surface supported multilayers as carriers for lipophilic cancer drugs to cells.[34] The feasibility of delivery of materials to cells from lipid multilayer patterns created with dip-pen nanolithography (DPN) has been established. DPN is a method that uses an atomic force microscope tip to deliver materials to a surface, with lateral resolution well below 1 micron. DPN can be carried out with parallel tip arrays for large area fabrication. Furthermore, multiple materials can be simultaneously delivered to a surface from different tips in parallel arrays, for instance using microfluidic channels to ink the tips, or microarray technology to deliver the different lipid inks to the AFM tips.

When carried out with lipid-based inks, DPN is capable of forming lipid multilayer nanostructures, where the multilayer thickness can be controlled. Multilayer thickness is particularly important for delivery applications because it allows encapsulation of materials such as drug candidates within the multilayers. Although DPN is well suited for prototype fabrication due to its ability to directly write arbitrary patterns, there are currently practical limits to its scalability for multi-material patterning. For instance, for small molecule microarray applications in drug screening, it would be desirable to have hundreds of thousands of different small molecules integrated onto a single surface. The ability for DPN to multiplex has been demonstrated for 24 different lipid inks,[35] but the scalability of that process has yet to be shown.

Lipid multilayer stamping uses a structured polymeric stamp to print lipid multilayer structures onto a surface.[22] It combines several aspects of well-established microfabrication methods in a new approach that is uniquely suited for lipid multilayer nanofabrication. In particular, lipid multilayer stamping combines the lateral patterning capabilities and scalability of microcontact printing[32], with the topographical control of nanoimprint lithography [36] to create nanostructured lipid multilayer arrays. A disadvantage of lipid multilayer stamping is that it requires pre-fabrication of a master, necessitating DPN to identify the optimal stamp geometry. Once that is determined, lipid multilayer stamping is a scalable method capable of mass production of lipid multilayer microarrays.

In one embodiment, the present invention provides the combination of scalable pin-spotting microarray technology with the process of lipid multilayer stamping in order to generate nanostructured lipid multilayer microarrays capable of screening liposomal formulations of a drug, such as the anticancer drug Docetaxel. In order to improve spot uniformity and scalability, an ink palette is used to ink the structured stamp. Since spots composed of lipid nanostructures are used in this technique, the term "stamped spot" refers to an area of the final patterned surface that originated from a single palette spot on the ink palette. The finer structures that make up each of the stamped spots are referred to as nanostructures, as the thickness of these structures is on the order of 10-100 nanometers with the lateral dimensions typically being several micrometers. In order to overcome the limitations of DPN and take advantage of the high throughput capabilities of microarray technology, lipid multilayer stamping may be employed. In this approach, lipids are arrayed onto a structured elastomeric stamp, which is then used to create lipid multilayer patterns. In order to make this invention applicable in a high throughput manner, microarraying techniques have to be adapted to increase the number of different materials that can be printed onto desired substrates using this stamping method.

In one embodiment, the present invention provides a device comprising: a lipid multilayer microarray suitable for screening of liposomal drug formulation on a chip; a method and apparatus for assaying for drug efficacy.

In one embodiment, the present invention provides a combination pin-spotting microarray technology with lipid multilayer stamping.

In one embodiment, the present invention provides a method to quantify cellular uptake of labeled materials.

In one embodiment, the present invention provides a method and apparatus of immersion of the array into a solution by adding the water in an inert atmosphere. For instance, a microwell plate could be sealed to contain an inert gas, and the solution injected into this atmosphere.

In one embodiment, the present invention provides a method and apparatus for simultaneously delivering different lipid-encapsulated materials in arrays.

In one embodiment, the present invention provides a method and apparatus for preventing cross-contamination of lipid-encapsulated materials in arrays.

In one embodiment, the present invention provides a method and apparatus for assaying for cell response to materials delivered from the microarray.

In one embodiment, the present invention provides a method and apparatus for localizing K562 leukemia cells from stamped drug-encapsulated lipid multilayers.

In one embodiment, the present invention provides a method of delivery of anticancer drug to leukemia cells from stamped drug-encapsulated lipid multilayers.

In one embodiment, the present invention provides a method for assaying the efficacy of lipid multilayer delivered drugs to leukemia cells.

In one embodiment, the present invention provides a method and apparatus for monitoring and controlling cell migration using fluorescently labeled lipid multilayers.

FIG. 1 depicts a general overview of a microarraying procedure 102 according to one embodiment of the present invention for creating lipid multilayer patterns that may have a nanometer resolution in height. As shown in step 110 of FIG. 1, a microarrayer (not shown in FIG. 1) deposits lipid inks 112 and 114 as palette spots 116 and 118, respectively on a palette 120. Palette spots 116 and 118 form a microarray on palette 120. After deposition, palette 120 is used to transfer lipid inks 112 and 114 from palette spots 116 and 118, respectively, to a topographically structured polymeric stamp 122, as shown in step 124. Stamp 122 includes a topographically structured surface 126 comprising ridges 130, 132, 134, 136, 138 and 140 and grooves 142, 144, 146, 148 and 150. Lipid ink 112 from palette spot 116 is forced into grooves 142 and 144. Lipid ink 114 from palette spot 118 is forced into grooves 148 and 150. At step 160, ink palette 120 is removed from stamp 122 so that at least some lipid ink 112 of palette spot 116 is retained in grooves 142 and 144 and so that at least some lipid ink 114 of palette spot 118 is retained in grooves 148 and 150. Palette 120 may be removed from stamp 122 by moving palette 120 away from stamp 122, by moving stamp 122 away from palette 120 or by moving palette 120 and stamp 122 away from each other. At step 164 stamp 122 is placed in contact with a substrate 166 to transfer lipid ink 112 in grooves 142 and 144 and lipid ink 114 in grooves 148 and 150 to substrate 166. At step 168, stamp 122 is removed from substrate 166 to form a patterned substrate 170 comprising substrate 166 and a patterned array 172 on substrate 166. Stamp 122 may be removed from substrate 166 by moving stamp 122 away from substrate 166, by moving substrate 166 away from stamp 122 or by moving stamp 122 and substrate 166 away from each other. Patterned array 172 comprises stamped spots 176, 178, 180 and 182. Stamped spots 176, 178, 180 and 182 are each a lipid microstructure. Stamped spot 176 is formed from lipid ink 112 in groove 142. Stamped spot 178 is formed from lipid ink 112 in groove 144. Stamped spot 180 is formed from lipid ink 114 in groove 148. Stamped spot 182 is formed from lipid ink 114 in groove 150. The spot volumes of stamped spots 176, 178, 180 and 182 on patterned substrate 170 are measured for quality control. After measuring stamped spots 176, 178, 180 and 182 for quality control, patterned array 172 of patterned substrate 170 is immersed in an aqueous solution containing cells at step 184 to deposit cells on patterned array 172. Cells 186 and 188 from the aqueous solution are shown deposited on patterned array 172 in step 190. Cells 186 and 188 have respective nuclei 192 and 194. Cells 186 and 188 are then be used to assay for liposomal drug efficacy in step 196.

Although in FIG. 1, the cells are shown being deposited on the patterned substrate by immersing the patterned array in an aqueous solution containing the cells, the cells may be deposited on the patterned substrate by other means. For example, the cells may be to deposit the cells in a dehydrated stated on the patterned substrate.

In one embodiment of the present invention, a cellular assay may involve detection of a cellular response to drug exposure and can include second messenger assays, reporter gene assays, cell proliferation assays, and high content screening. Second messenger assays monitor signal transduction from activated cell-surface receptors that can measure fast transient fluorescent signals. Reporter gene assays monitor cellular responses at the transcription/translation level, which indicate the presence or absence of a gene product that reflects changes in a signal transduction pathway. Cell proliferation assays are quick and easily employed for automation because they measure the overall growth, no growth, or death responses of the cell to external stimuli. Lastly, high content screening analyzes cells using fluorescence based reagents that yield multi-parametric measurements of subcellular events. For example, measurement of apoptosis that provides information such as nuclear size and morphological changes, nuclear DNA content, mitochondrial potential, and actin-cytoskeletal rearrangements during drug-induced programmed cell death.[40]

Figure 2:
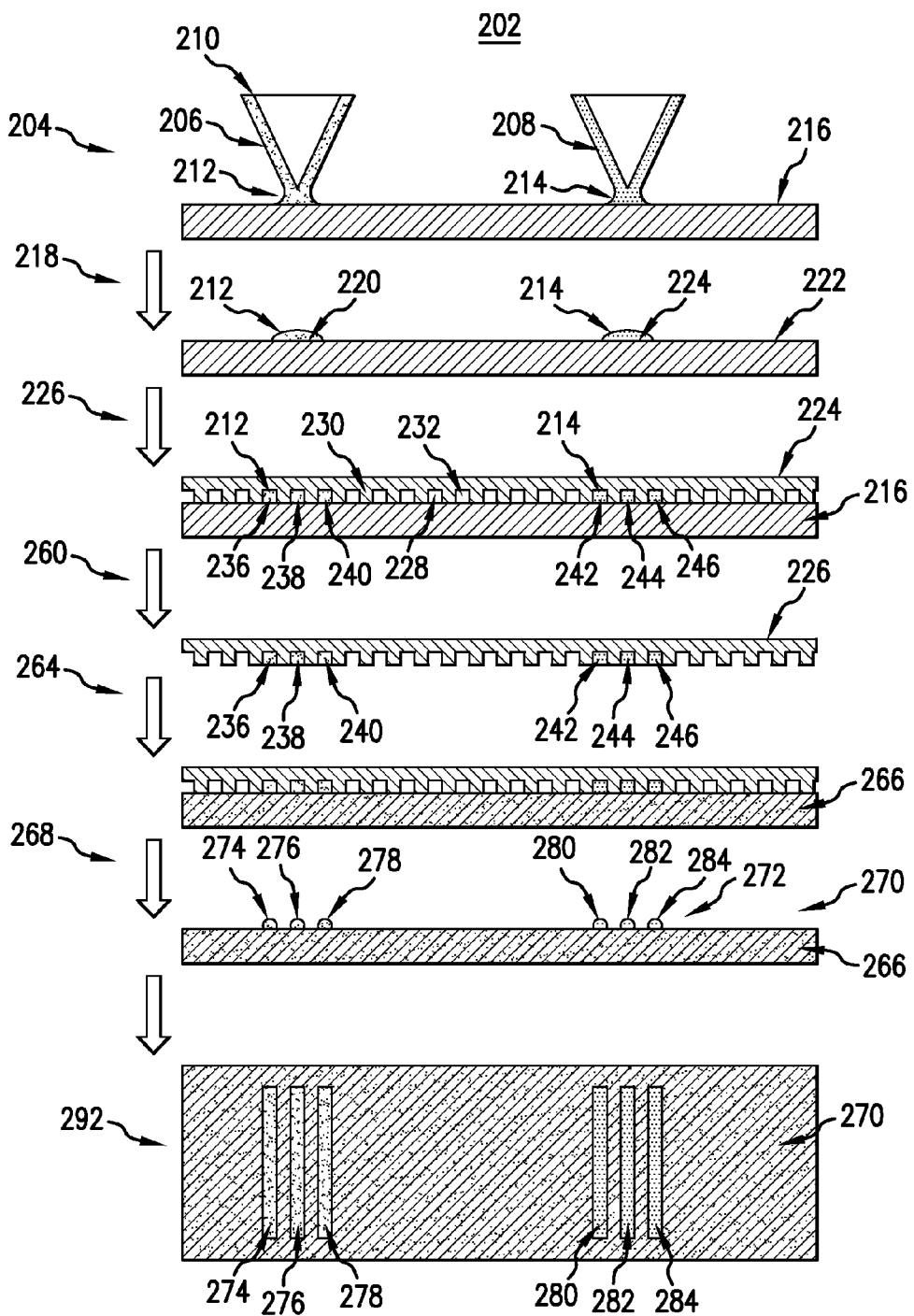
FIG. 2 is a schematic illustration of the process of scalable lipid multilayer stamping.

FIG. 2 depicts a general overview of a microarraying procedure 202 according to one embodiment of the present invention. As shown in step 204 of FIG. 2, tips 206 and 208 of a microarrayer 210 deposit respective lipid inks 212 and 214 on a palette 216. At step 218, microarrayer 210 is removed from palette 216 leaving palette spots 220 and 222 on palette 216. Microarrayer 210 may be removed from palette 216 by moving microarrayer 210 from palette 216, by moving palette 216 away from microarrayer 210 or by moving microarrayer 210 and palette 216 away from each other. Palette spot 220 consists of lipid ink 212. Palette spot 222 consists of lipid ink 214. Palette spots 220 and 222 spots form a microarray on palette 216. After deposition, palette 216 is used to transfer lipid inks 212 and 214 to a topographically structured polymeric stamp 224, as shown in step 226. Stamp 224 includes a topographically structured surface 228 comprising ridges 230 and grooves 232. Lipid ink 212 from palette spot 220 is forced into grooves 236, 238 and 240 of grooves 232. Lipid ink 214 from palette spot 222 is forced into grooves 242, 244 and 246 of grooves 232. At step 260, ink palette 216 is removed from stamp 224 so that at least some lipid ink 212 of palette spot 220 is retained in grooves 236, 238 and 240 and at least some lipid ink 214 of palette spot 222 is retained in grooves 242, 244 and 246. Palette 216 may be removed from stamp 224 by moving palette 216 away from stamp 224, by moving stamp 224 away from palette 216 or by moving palette 216 and stamp 224 away from each other. At step 264 stamp 224 is placed in contact with a substrate 266 to transfer lipid ink 212 in grooves 236, 238 and 240 and lipid ink 114 in grooves 242, 244 and 246 to substrate 266. At step 268, stamp 224 is removed from substrate 266 to form a patterned substrate 270 comprising substrate 266 and a patterned array 272 on substrate 266. Stamp 224 may be removed from substrate 166 by moving stamp 224 away from substrate 266, by moving substrate 266 away from stamp 224 or by moving stamp 224 and substrate 266 away from each other. Patterned array 272 comprises stamped spots 274, 276, 278, 280, 282 and 284. Stamped spots 274, 276, 278, 280, 282 and 284 are each a lipid microstructure. Stamped spot 274 is formed from lipid ink 212 in groove 236. Stamped spot 276 is formed from lipid ink 212 in groove 238. Stamped spot 278 is formed from lipid ink 212 in groove 240. Stamped spot 280 is formed from lipid ink 214 in groove 242. Stamped spot 282 is formed from lipid ink 214 in groove 244. Stamped spot 284 is formed from lipid ink 214 in groove 246. The spot volumes of stamped spots 274, 276, 278, 280, 282 and 284 on patterned substrate 270 are measured for quality control. As can be seen in view 292, spots 274, 276, 278, 280, 282 and 284 are elongated in shape.

Although in FIGS. 1 and 2 for simplicity of illustration all of the lipid ink in each of the spots is shown being forced into the grooves of the stamp, in other embodiments of the present invention, there may be much more lipid ink in the spots than is forced into the grooves of the stamp. For example, by providing more lipid ink in each of the spots of a palette, the palette may be used to print patterned arrays several substrates.

The lipid multilayer structures used in the arrays of the present invention may be microstructures or nanostructures. When cells are deposited on the patterned substrate, it is sometimes important that the stamped spots be smaller than each of the cells, so that the cells can adhere to the patterned substrate. However, for some types of cells, larger spots may be used. For example, a suspension cell, such as the K652 cells shown in FIG. 33 may be adhered to patterned substrates having larger spots.

Microarraying lipid inks onto a polymeric ink palette increases the uniformity of lipid deposition from a microarrayer. Microarraying lipid inks on a palette also aids in the eventual deposition of lipids inks on the substrate by ensuring there is no excessive or inadequate ink deposition on the substrate. In addition ink palette with lipid inks arranged in a microarray may be used in order to ink multiple arrays. Microarraying technology enables lipid deposition to be controlled in a way such that creates a known array of multiple different lipid inks (multiplexing).

In addition to forming a microarray using pin spotting as shown in FIG. 2, other types of microarray technology may also be employed to form a microarray of the present invention. For example, a microarray of the present invention may be formed using inkjet printing, dip-pen nanolithography, etc.

In one embodiment of the present invention, each of the spots of the microarray of spots on the palette may be 0.01 to 5000 μm in diameter.

In one embodiment of the present invention, multilayer stamping in the form of 5 micrometer diameter dot patterns allows for sub-micron control of the lipid pattern thickness cross-sectional area.

Figure 3:
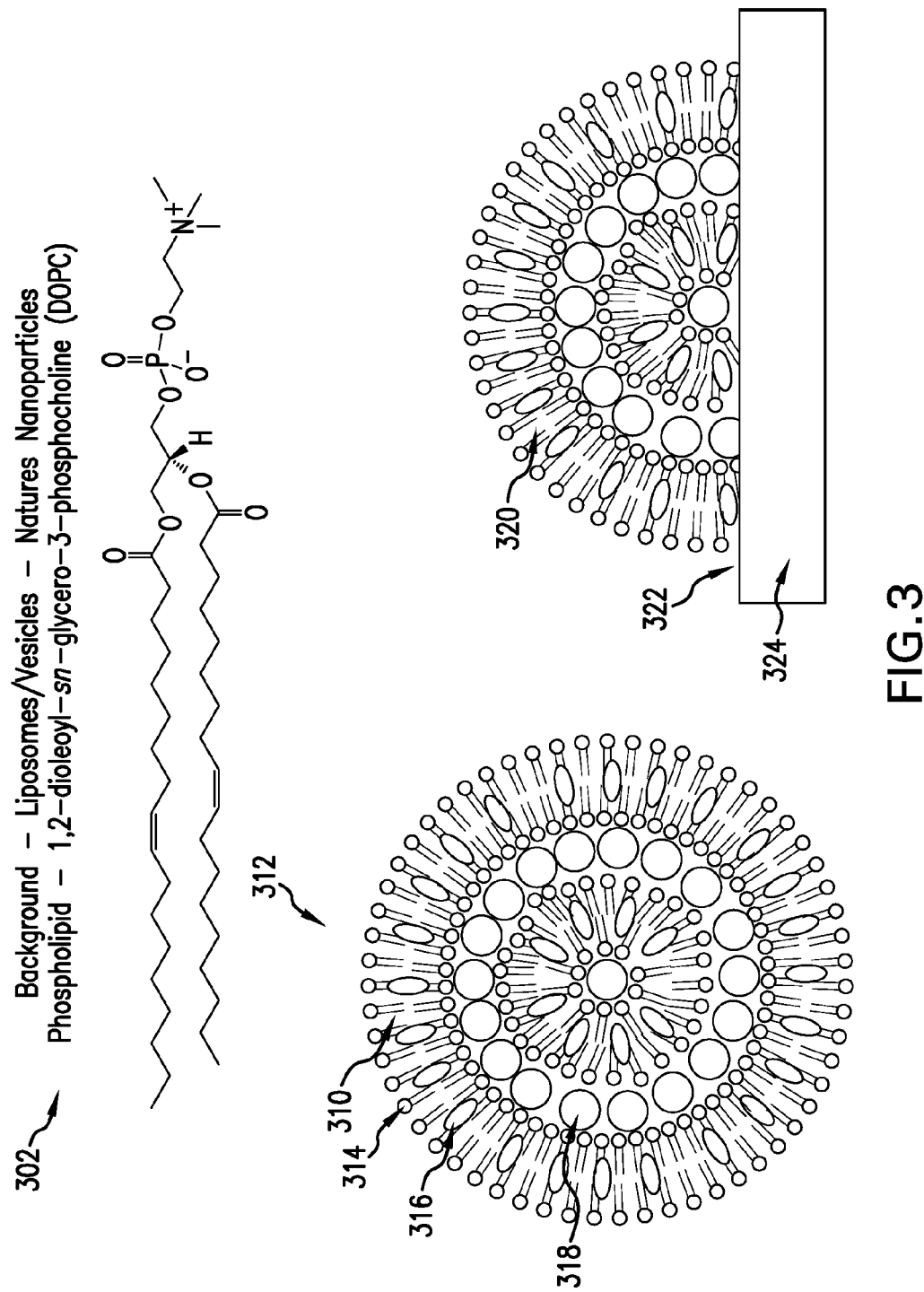
FIG. 3 is a diagram showing chemical and supramolecular structures of liposomes and surface-supported loaded lipid nanostructures and the chemical structure of 1,2-dioleoyl-3-trimethylammoniumpropane (chloride salt) (DOTAP).

FIG. 3 shows chemical and supramolecular structures of liposomes and surface-supported lipid nanostructures. The chemical structure of 1,2-dioleoyl-sn-glycero-3-phosphocholine (DOPC), a typical phospholipid that may be used in lipid microstructure of the present invention, is indicated by arrow 302. FIG. 3 also shows one example of one type of liposome supramolecular structure that self-assembles in water 312, i.e., multilamellar liposome 310 that is comprised of DOPC 314, non-polar drug molecule 316 and polar drug molecule 318. FIG. 3 also shows a surface-supported lipid multilayer liposome 320 on a surface 322 of substrate 324. FIG. 3 shows one possible supramolecular structure and serves the purpose of comparing the structure of liposomes in solution with surface-supported liposomes or lipid multilayer nanostructures.

Figure 4:
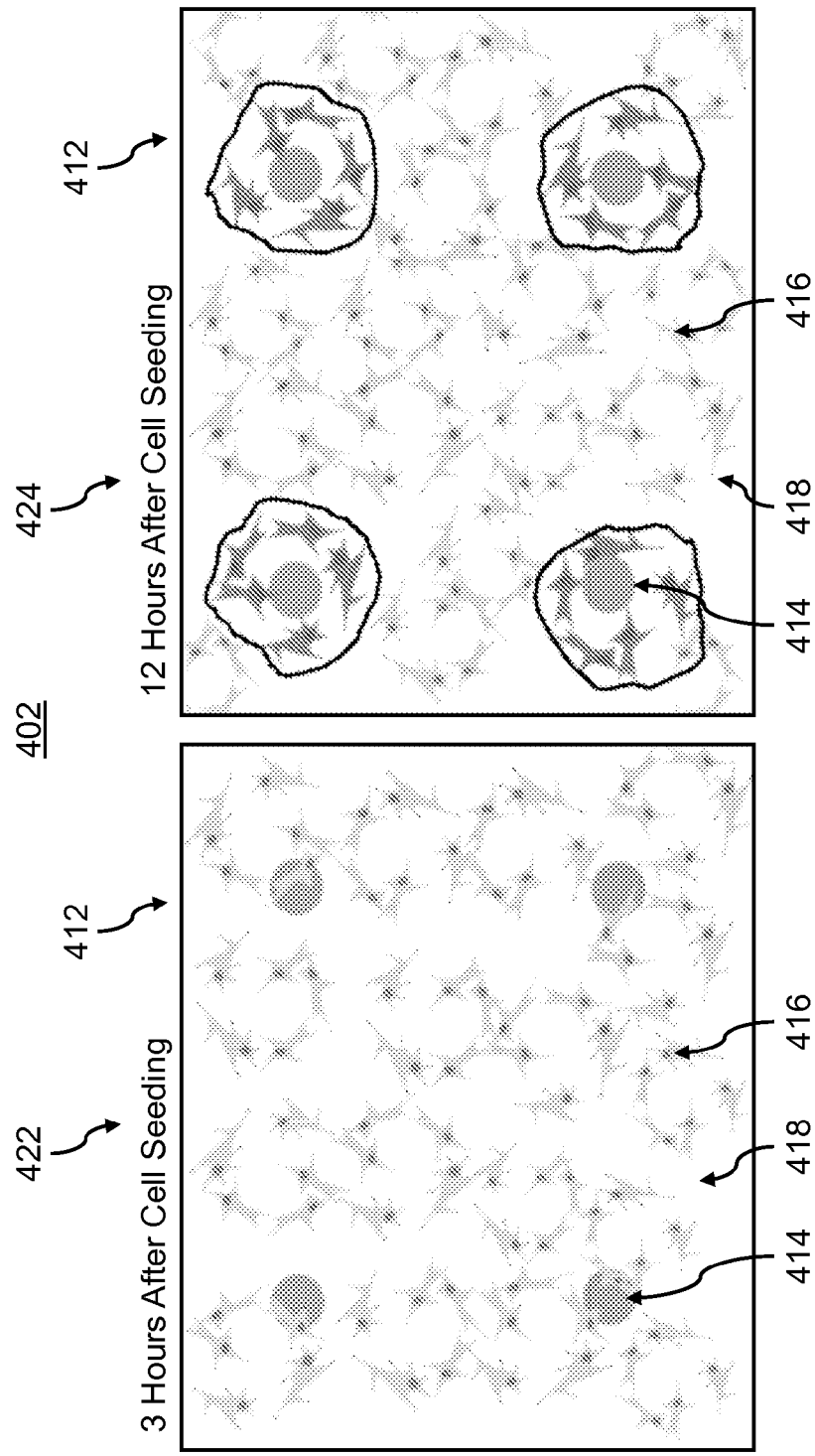
FIG. 4 illustrates an assay for cell migration that measures how far motile cells migrate from spots on a microarray.

FIG. 4 shows expected observation of cells that have been cultured on an array and allowed to migrate from the microarray spots. FIG. 4 shows a migration array assay 402 according to one embodiment of the present invention using an array 412 of array spots 414 covered with cells 416. Array spots 414 are deposited on a substrate 418 using a microarraying technique of the present invention such as described above and shown in FIGS. 1 and 2. Cells 416 are "seeded,"

i.e., are deposited on top of array spots 414 of array 412. Illustration 422 shows array 412 three hours after cell seeding. Illustration 424 shows array 412 twelve hours after cell seeding.

In one embodiment of the present invention, the topographically structured stamp may be a stamp made of polydimethylsiloxane (PDMS). Such a stamp may be made by pouring liquid PDMS over a silicon master. Other materials that may be used for a topographically structured stamp of the present invention include materials such as various types of plastics, various types of rubber, etc.

The patterned substrates of the present invention may be used in a variety of cellular assay methods. In one embodiment, an assay method of the present invention comprises the following steps: (1) Cells are seeded on the array; (2) Cells are allowed to grow; (3) The cells are stained (optional); and (4) Cells are counted and the number of cells on each spot is used as a measure of viability. In other embodiments of the present invention, steps 3 and 4 are replaced by second messanger assays, reporter gene assays, or high content screening methods

EXAMPLES

Materials
Chemical Structures

Figure 5:
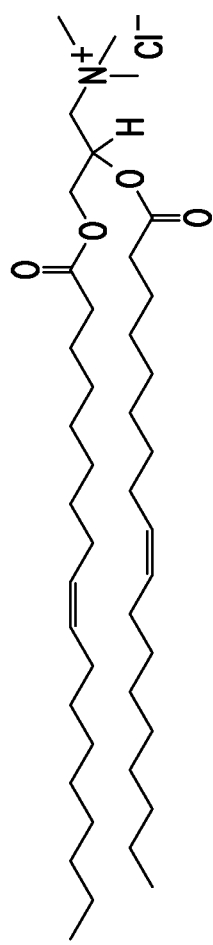
FIG. 5 shows the chemical structure of 1,2-dioleoyl-3-trimethylammonium-propane (chloride salt) (DOTAP).
Figure 6:
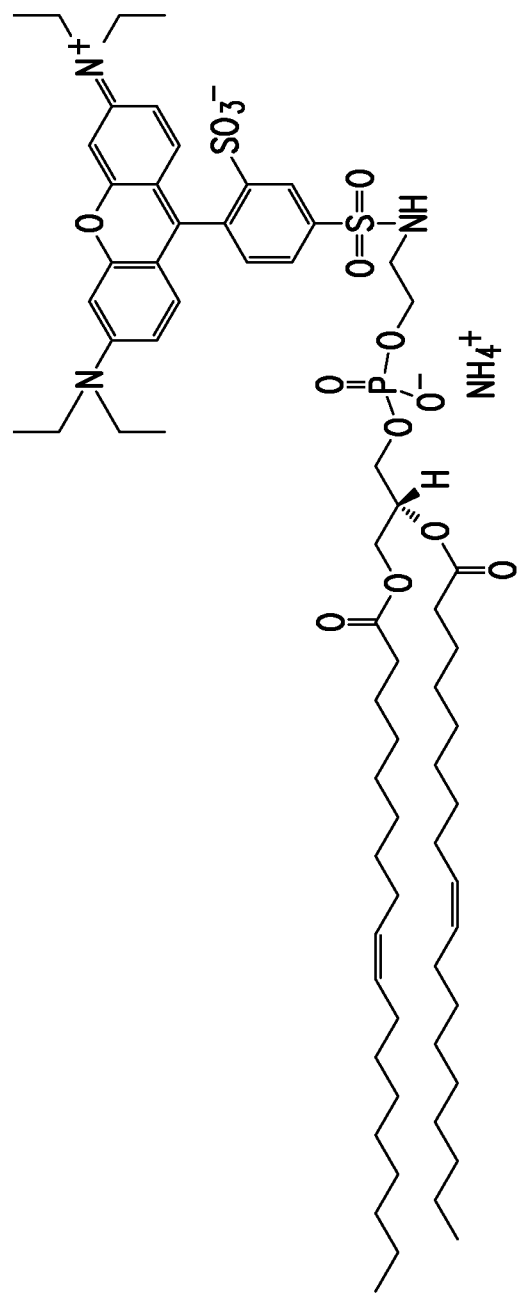
FIG. 6 shows the chemical structure of 1,2-dioleoyl-sn-glycerol-3-phosphoethanolamine-N-(lissamine rhodamine b sulfonyl) (ammonium salt) (DOPE-rhodamine).
Figure 7:
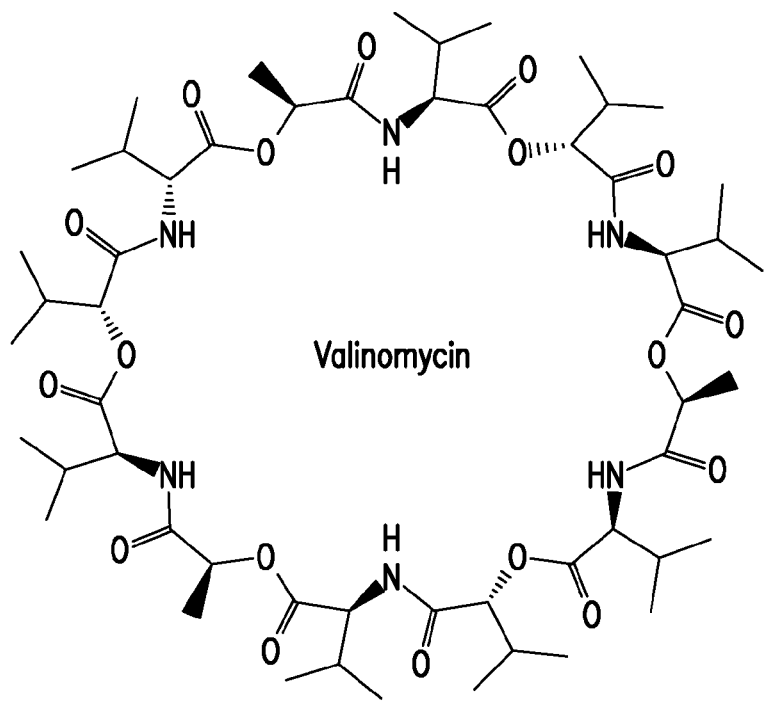
FIG. 7 shows the chemical structure of valinomycin.
Figure 8:
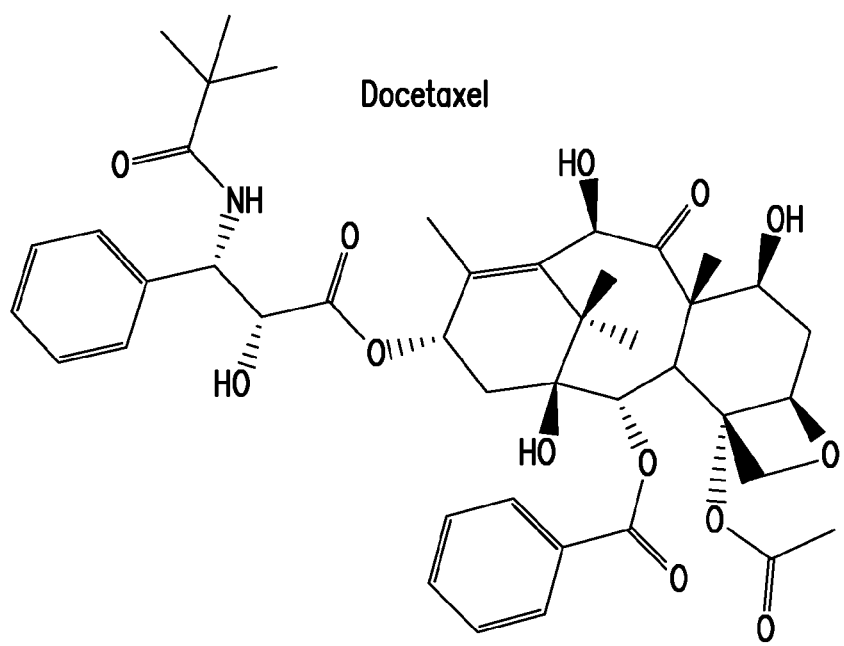
FIG. 8 shows the chemical structure of Taxotere® (docetaxel).

FIG. 5 shows the chemical structure of 1,2-dioleoyl-3-trimethylammonium-propane (chloride salt) (DOTAP). FIG. 6 shows the chemical structure of 1,2-dioleoyl-sn-glycerol-3-phosphoethanolamine-N-(lissamine rhodamine b sulfonyl) (ammonium salt) (DOPE-rhodamine or DOPE-RB). FIG. 7 shows the chemical structure of valinomycin. FIG. 8 shows the chemical structure of Taxotere® (docetaxel). DOTAP, DOPE-rhodamine, valinomycin and docetaxel are used in various examples below.

Liposome Ink Preparation

The lipids used for arraying and screening were 1,2-dioeoyl-snglycero-3-phosphocholine (DOPC), 1,2-dioleoyl-3-trimethylammonium-propane (chloride salt) (DOTAP), 1,2-dioleoyl-sn-glycero-3-phosphoethanolamine-N-lissamine rhodamine B sulfonyl (DOPE-RB). These lipids were purchased from Avanti Polar Lipids, Inc. 1,2-dihexadecanoyl-snglycero-3-phosphoethanolamine (Marina Blue DHPE) was purchased from Invitrogen. Solutions were prepared by mixing chloroform solutions of the different lipids to obtain the desired molar ratios. The chloroform was then evaporated off under a Nitrogen stream, followed by allowing the samples to dry further in the vacuum overnight in order to form a thin film of lipids on the bottom of the glass vials. After drying, water was added to the vials containing the dried lipid material and the samples were then lightly vortexed for 10 seconds and then sonicated for 10 minutes. Further vortexing after sonification was utilized as needed to ensure suspension of lipids in water.

Multiplexing

DOTAP was doped with 1 Mol % rhodamine-PE, Marina Blue DHPE and carboxyfluorescein,-PE, respectively and were microarrayed in a 3×3 array pattern onto a PDMS ink pallet. The microarray pins were subjected to various wash times in order to determine the extent of any cross contamination between the two different lipid inks.

Microarraying

The different lipid solutions were microarrayed using a BioRobotics pinspotter model BG600 (Comberton, Cambridge, England) onto the desired substrate of choice, using a 200 micron 4×4 stainless steel solid pin tool.

Multilayer Stamping

DOTAP stamping was inked using the microarraying procedure onto an ink palette. Water was evaporated from the ink palette by leaving the sample in the vacuum overnight. The PDMS stamp was then inked by being placed into firm, uniform contact with the ink pallet. Once the PDMS stamp was inked, it was stamped onto a glass substrate. Uniform, firm pressure was applied to the stamp for ~20 seconds before careful removal from the surface.

Surfaces Used and Sample Preparation

γ-irradiated and Poly-d-lysine-coated Glass bottom Culture Dishes were obtained from MatTek Corporation. No. 1.5 mm, 22×22 mm coverslip substrates not used for cell culture were obtained from VWR and used straight out of the box.

Characterization and Imaging Techniques

A Ti-E epifluorescence inverted microscope (Nikon Instruments, Melville, N.Y.) fitted with a Retiga SRV (Qlmaging, Canada) CCD camera (1.4 MP, Peltier cooled to −45° C.) was used for fluorescence and brightfield imaging of the lipid nanostructures on glass surfaces. The heights and topography of the lipid prints were measured using tapping mode with a Dimension 3000 AFM (Veeco Instruments, Plainview, N.Y.) and tapping mode AFM cantilevers (#OMCLAC160TS-W2, 7 nm nominal tip radius, 15 μm tip height, 42 N m−1 spring constant, Olympus, Center Valley, Pa.). Noncontact mode AFM imaging is suitable for imaging micro- and nanoscopic fluid droplets.[39]

Miscellaneous Materials

Microarrayer, PDMS stamps (flat PDMS without wells on either surface, 5 μm, 1 μm wells), vacuum desiccators, DOTAP, DOPE, drugs (valinomycin, Taxotere), cells (HEK 293, HeLa, NIH 3T3), humidity chamber.

Stamp Printing

Lipid formulations were printed onto flat PDMS inkpad using the microarrayer with 800 μm spacing between the spots to be used as an inking pad. A PDMS stamp with 5 μm wells was then pressed against the inking pad. This was then placed in a vacuum overnight to remove any residual water from the wells. The stamp was then placed on a plasma-cleaned glass with the patterns against the glass slide and kept in a humidity chamber for 2 hours before being used for stamping.

Multilayer Stamping

The lipid dot pattern arrays were printed by placing the printed face of the inked PDMS stamp onto the substrate (glass) and pressing firmly against the substrate. Discernible patterns were achieved after the first few prints got rid of excess inking on the stamp.

Cell Culture

Introduction of the cells onto the patterned slide was done in a simple glove box with a low nitrogen stream with humidity at 10%. 500,000 cells were seeded into each well of the six-well plates to obtain 70% confluence over the pattern areas. The cells were incubated at 37° C. for 24 hours and 5% $CO_2$ Cells were assayed for viability.

Viability Assays

Cell viability was determined using the BacLight viability assay from Invitrogen®.

Example 1

Lipid multilayer stamping techniques of the present invention, when combined with microarray technology should allow for the increase in throughput of printing. Coating of PDMS stamps has been done by dipping in a solution of the desired material or by the peeling method where the stamp is put on a drop of the material and peeled off.[7] Using arrays of surface-supported liposomes for small molecule microarray screening is a very novel approach. FIGS. 9, 10, 11, 12, 13 and 14 show an illustration of liposomal structures in solution (state of the art) and on a surface using techniques of the present invention. These structures have similarities to solution based liposomes, which are well established lipid-based drug-delivery systems[37], especially for drugs that may be may be insoluble in water[6]. Fundamental differences include: (1) the ability to test multiple different materials on cells within the same solution by means of the microarray concept and (2) the micro and nanostructure can be readily characterized by optical and atomic force microscopy as the lipids are confined to a surface.

Figure 9:
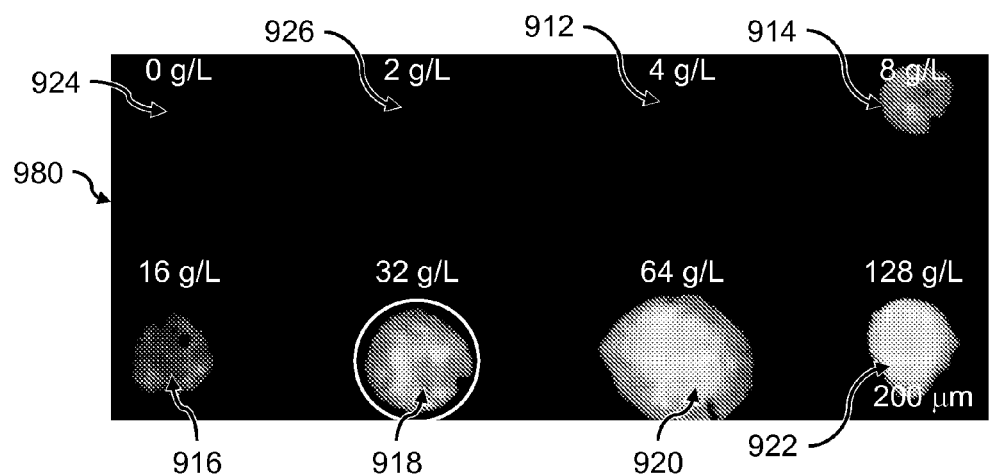
FIG. 9 shows a 4× red fluorescent image of Lipid Dot Patterns created from microarraying and multilayer stamping using a 5 μm well pattern at varying concentrations of DOTAP.

Characterization of lipid patterns were initially carried out with the cationic lipid, 1,2-dioleoyl-3-trimethylammonium-propane (chloride salt) (DOTAP). FIG. 9 shows a 4× red fluorescence image lipid patterning on glass substrate 980 for a series of DOTAP concentrations doped with 1 Mol % rhodamine. Liposomal concentrations of 4 (912), 8 (914), 16 (916), 32 (918), 64 (920) and 128 (922) g/L provided adequate microarray deposition onto a PDMS ink palette. A liposomal concentration of 2 g/L (926) was used, but failed to provide adequate transfer, just like control 924. The lipid patterns shown were created on the fourth print. Generally, higher concentrations require more preliminary prints in order to remove excess ink from the PDMS stamp.

Figure 10:
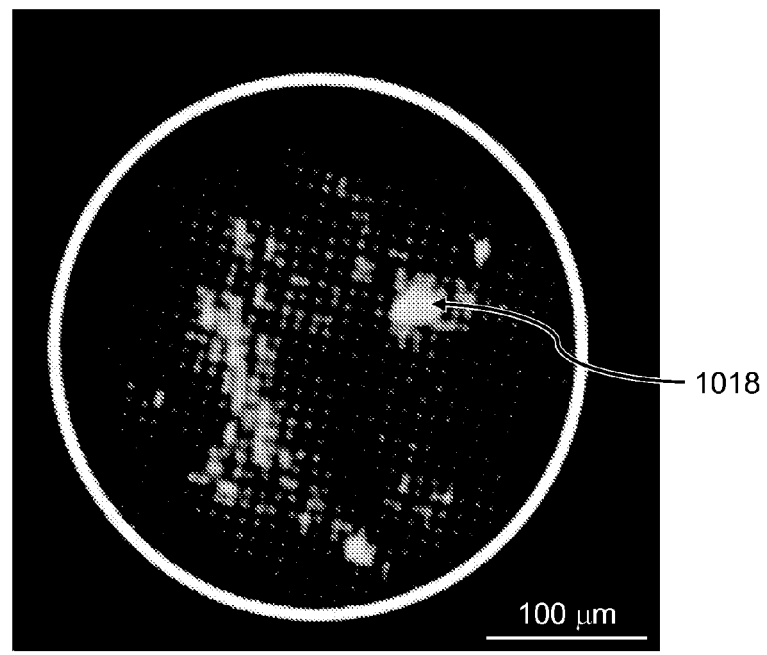
FIG. 10 is a fluorescent image of the lipid dot pattern created from 32 g/L concentration shown in FIG. 8.

FIG. 10 is a panel showing a 10× red fluorescence image of a DOTAP nanopattern created from the liposomal concentration of 32 g/L 1018. Non-uniform regions are shown, as well as uniform dots in the pattern.

Figure 11:
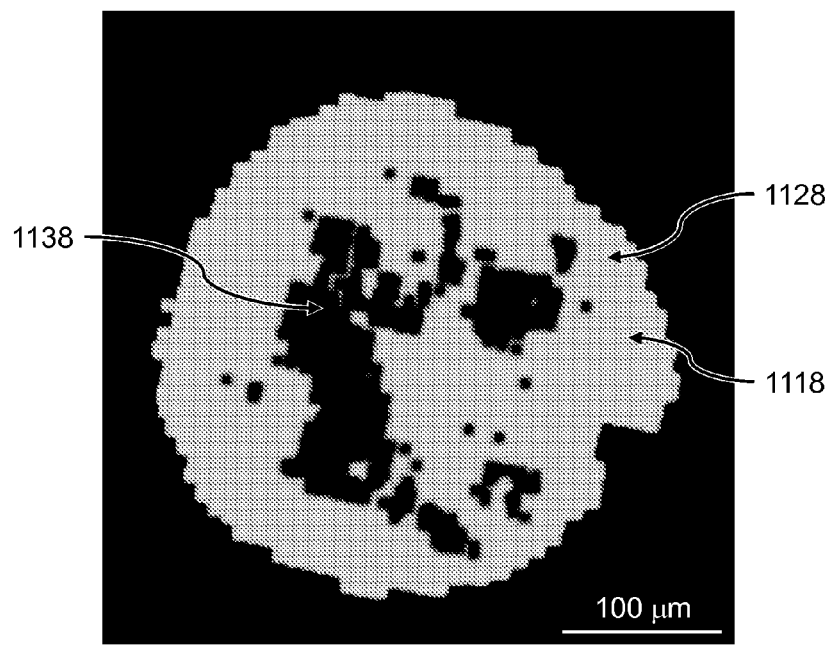
FIG. 11 is an imageJ analysis of thresholded mask regions of the non-uniform regions (colored red) of the pattern and the total area of the pattern (colored green), respectively.

In order to characterize this, an imageJ macro was created to measure the entire area of the lipid pattern and the non-uniform regions as shown in FIG. 11. The macro creates a mask and then dilates the pixels of the pattern to create a total area. Output 1118 is the total area in pixels and a picture, which is shown in FIG. 11 as green. The macro then repeats but first erodes the pixels to erase the uniform regions 1128, then dilates the same amount of times in order to show only non-uniform regions 1138, which in FIG. 11 is red. The inked PDMS stamp will eventually print numerous uniform lipid dot patterns while it is adequately inked.

Figure 12:
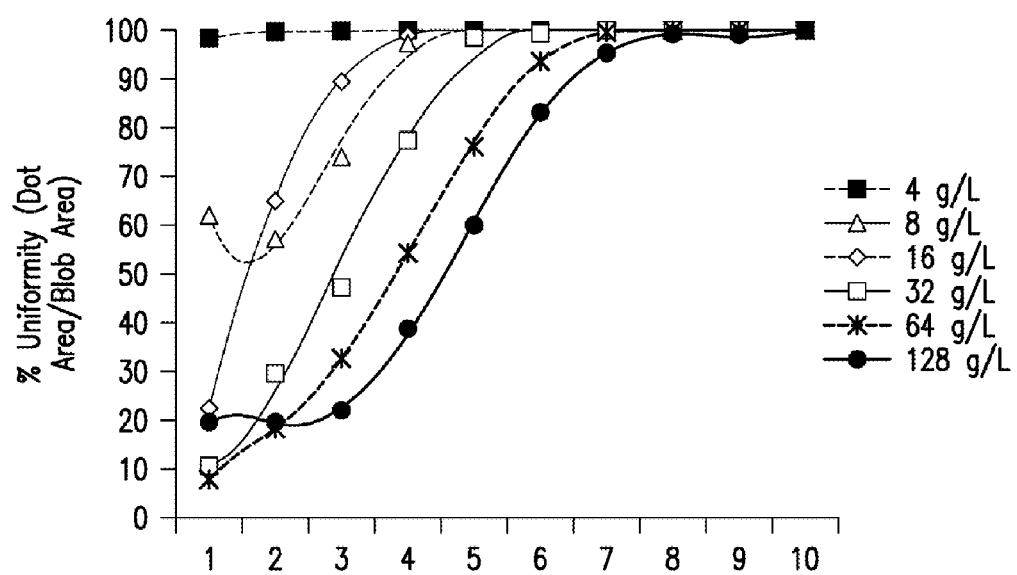
FIG. 12 is a graph showing the uniformity characterization obtained from the analytical technique shown in FIG. 10.

FIG. 12 is a graph showing the increase in uniformity as the number of successive prints increase. The data was obtained by the process shown in FIG. 11 for each print. Percent uniformity of the entire lipid pattern is defined as [1—(non-uniform regions/total area)]×100%.

Figure 13:
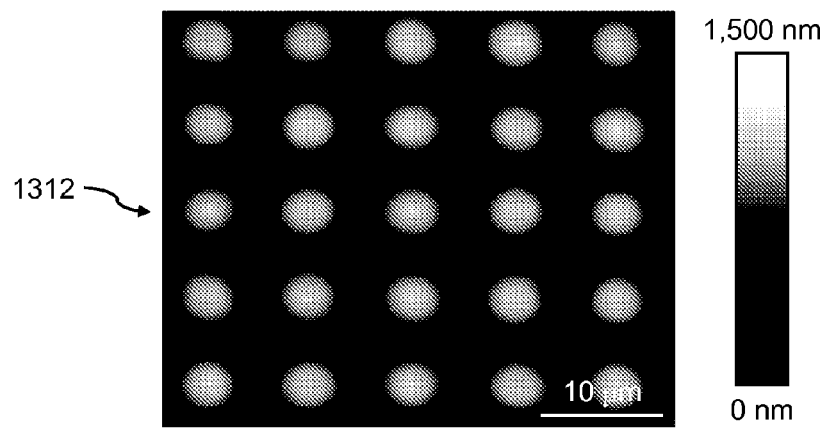
FIG. 13 is an image showing the AFM height profile of 25 lipid dots imaged on glass derived from a liposomal concentration of 16 g/L.

FIG. 13 shows another experiment where the same liposomal concentrations were again microarrayed and stamped onto glass substrate 1312. Each of the lipid patterns were imaged using AFM. A sample of 25 lipid dots from each pattern created from the different liposomal concentrations were imaged and analyzed to determine the height of each dot. FIG. 13 shows an example AFM image of the 16 g/L liposomal concentration.

Figure 14:
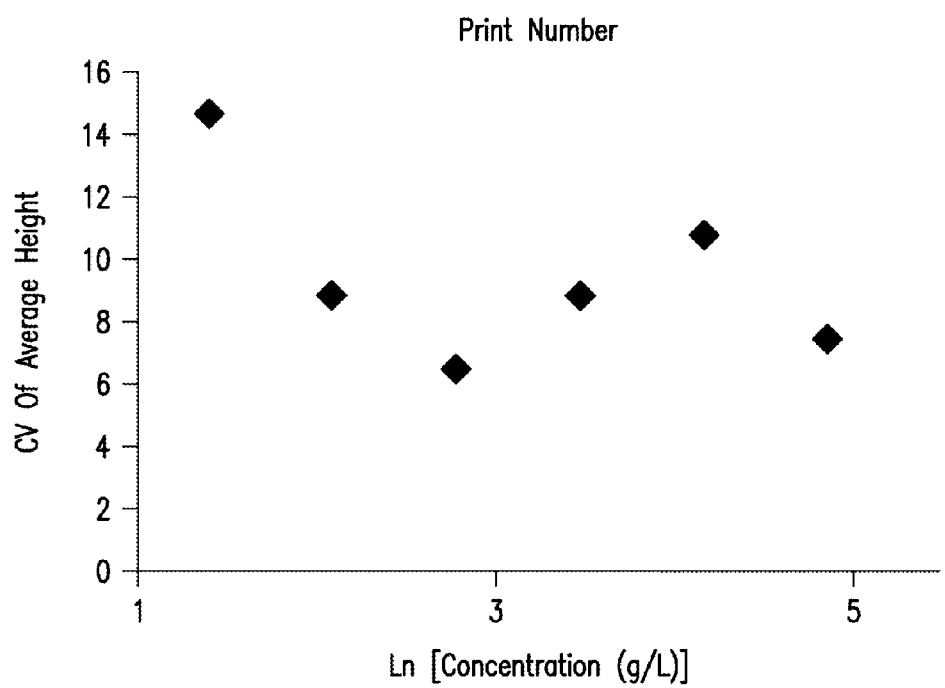
FIG. 14 is a graph showing the average height of lipid dots derived from the series of AFM measurements on glass as shown in FIG. 13.
Figure 15:
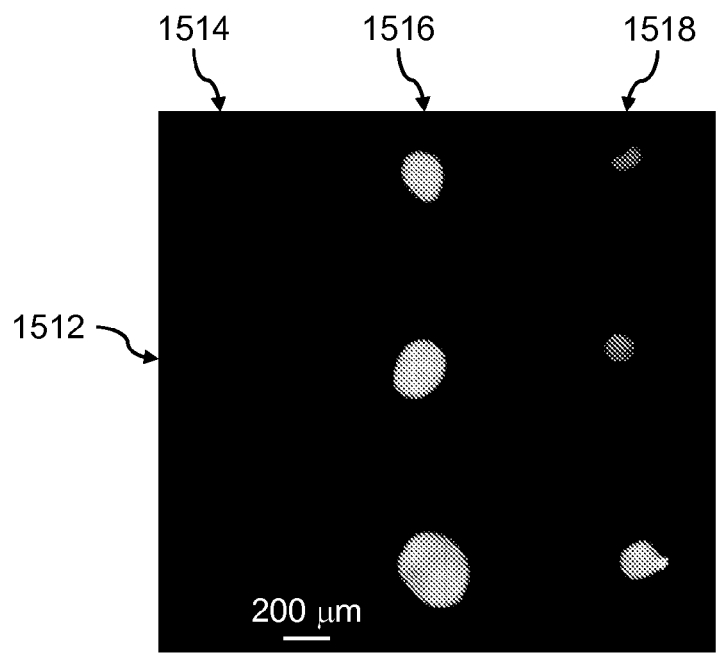
FIG. 15 is an image of a 3×3 ink pallet of DOTAP-doped with 1 Mol % Marina Blue-DHPE, Rhodamine-DOPE and Carboxyfluorescein-DOPE.

Using imageJ, round Regions of Interest were formed around each of the lipid dots and the average intensity was calculated. Using the AFM image height conversion, the average height of each of the 25 lipid dots were found. FIG. 14 shows the CV of the heights, such that CV=standard deviation of average height/mean average height×100% plotted with the concentration of each liposomal concentration from which the surface structures were derived.

Example 2

Figure 16:
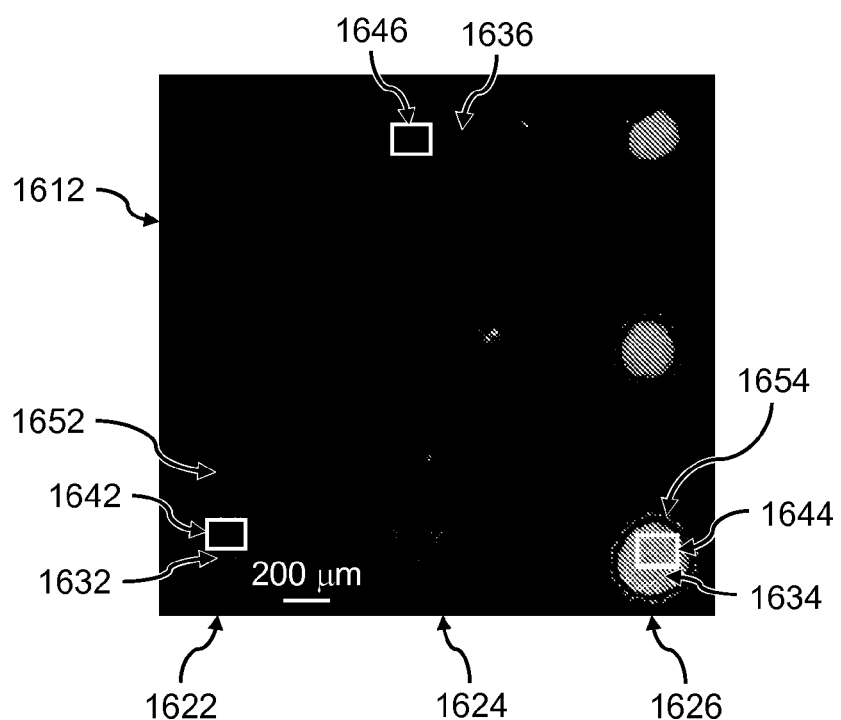
FIG. 16 is a 10× fluorescence stitch image of lipid dot patterns structured from the different lipid inks that were multilayer stamped onto a glass slide.
Figure 17:
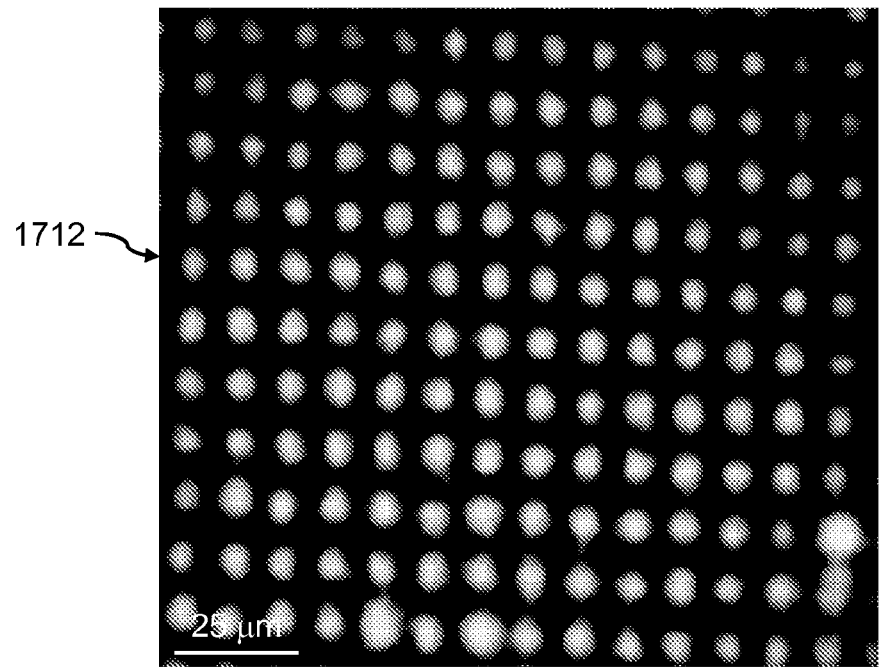
FIG. 17 is a digitally zoomed image of Marina Blue-DHPE doped patterns shown in FIG. 10.
Figure 18:
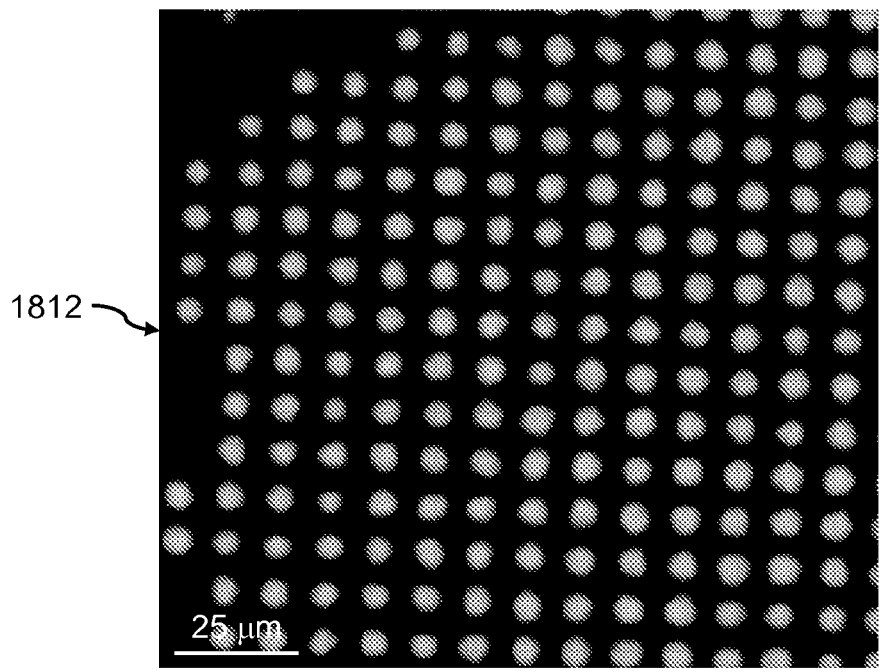
FIG. 18 is a digitally zoomed imaged of Rhodamine-PE doped patterns shown in FIG. 10.
Figure 19:
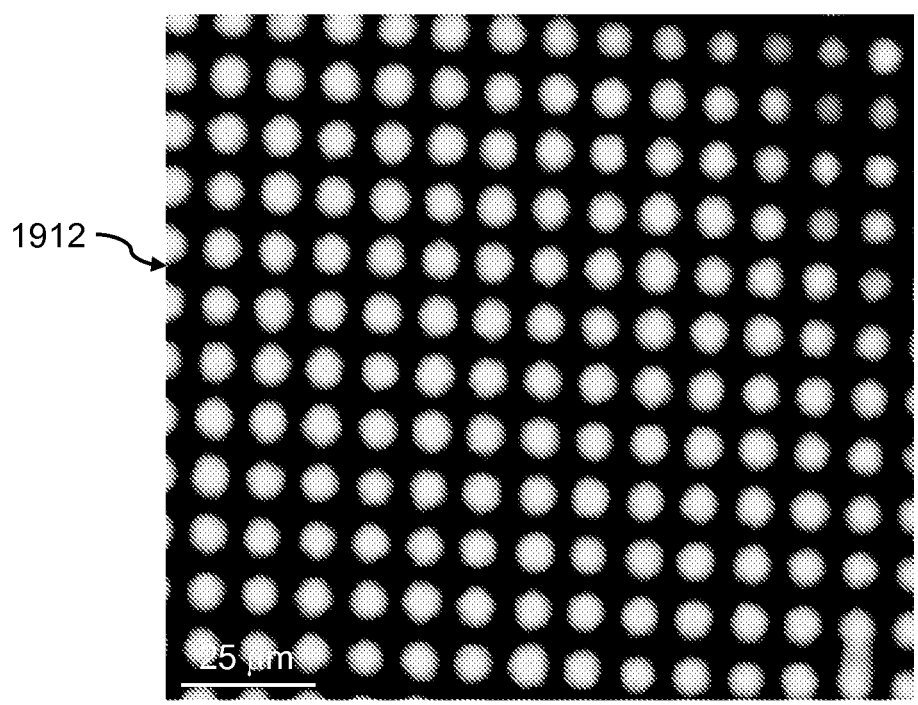
FIG. 19 is a digitally zoomed image of Carboxyfluorescein-PE doped patterns shown in FIG. 10.

FIGS. 15, 16, 17, 18 and 19 represent the multiplexing capabilities of a microarraying process in combination with multilayer stamping according to one embodiment of the present invention. The microarrayer is capable of writing multiple inks onto the same substrate, as shown in panel 1512 of FIG. 15. The three different fluorophores used in the test shown in FIG. 15 were Marina Blue-DHPE (a blue fluorophore), carboxyfluorescein-pe (a green fluorophore) and rhodamine-pe (a red fluorophore), which were used in columns 1514, 1516 and 1518, respectively. With the washing protocol used, there was no cross contamination observed in this sample. Panel 1612 of FIG. 16 shows the ability of multilayer stamping according to one embodiment of the present invention to faithfully produce lipid dot patterns of DOTAP doped with different fluorophores. The fluorophores used in the test in FIG. 16 were Marina Blue-DHPE (column 1622), carboxyfluorescein-pe (column 1624) and rhodamine-pe (column 1626). FIG. 16 shows lipid dot patterns 1632, 1634 and 1636 and white boxed regions 1642, 1644 and 1646. Halos 1652 and 1654 around the blue and green fluorophores, respectively, are spread cationic multilayers that result from the stamping process and subsequent exposure to environmental conditions. Panels 1712, 1812 and 1912 of FIGS. 17, 18 and 19, respectively, show digitally zoomed 4× fluorescence micrographs of the three different lipid dot patterns shown FIG. 16, i.e., lipid dot patterns 1632, 1634 and 1636, respectively. FIGS. 17, 18 and 19 show white boxed regions 1642, 1644 and 6146, respectively, of FIG. 16.

Example 3

Figure 20:
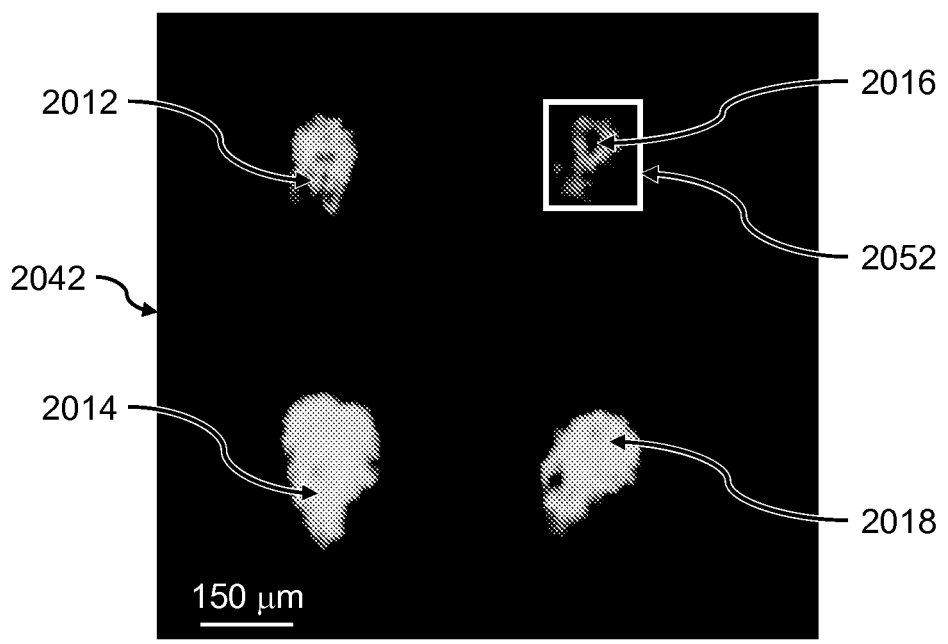
FIG. 20 is a 4× TRITC fluorescence micrograph of patterns of DOTAP multilayers printed onto glass using a 5 μm well stamp.
Figure 21:
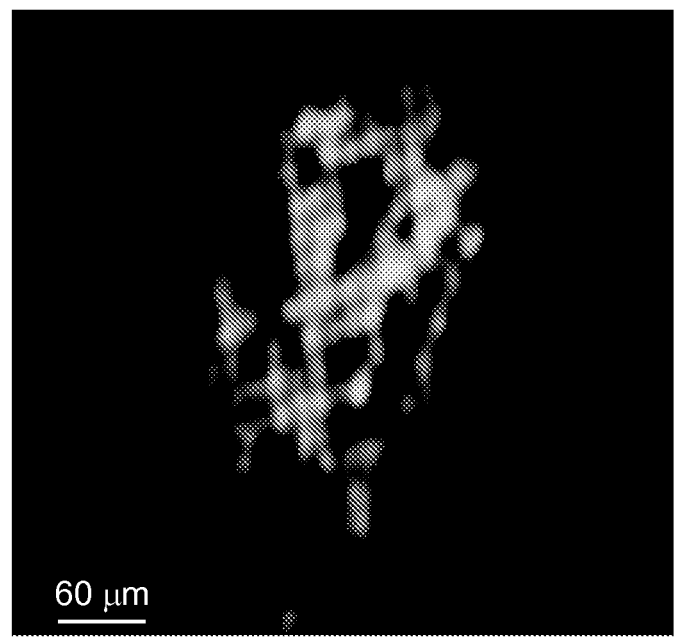
FIG. 21 is an image showing the digital zoom of spot in FIG. 14 indicated with the white square.
Figure 22:
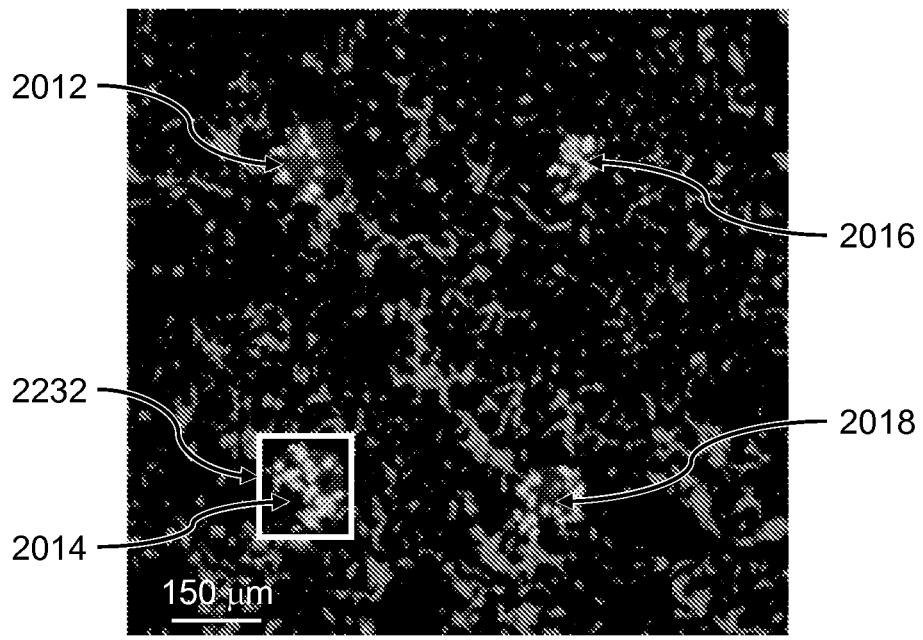
FIG. 22 is a 4× merged fluorescence micrograph of FITC and TRITC images of spots in FIG. 14.
Figure 23:
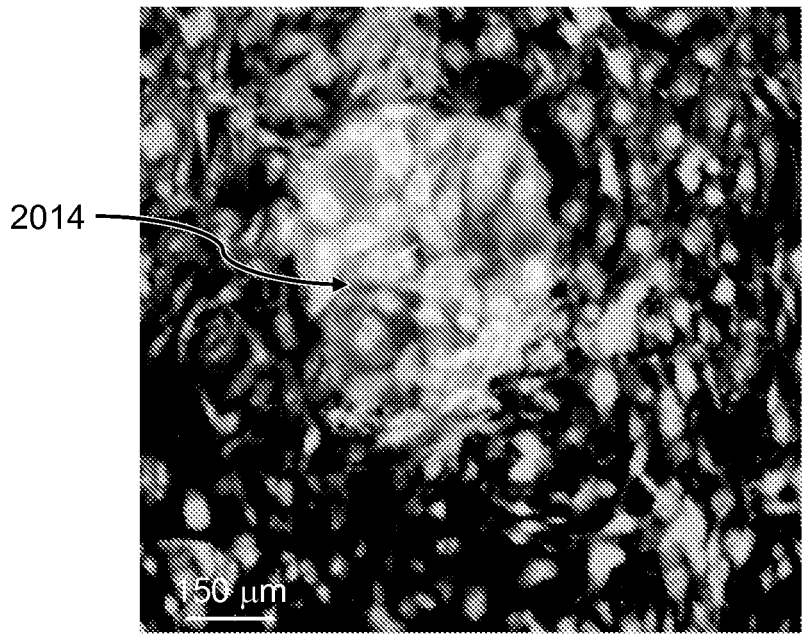
FIG. 23 is a 10× merged fluorescence micrograph of FITC and TRITC images of a spot in a region indicated by a white box in FIG. 16.
Figure 24:
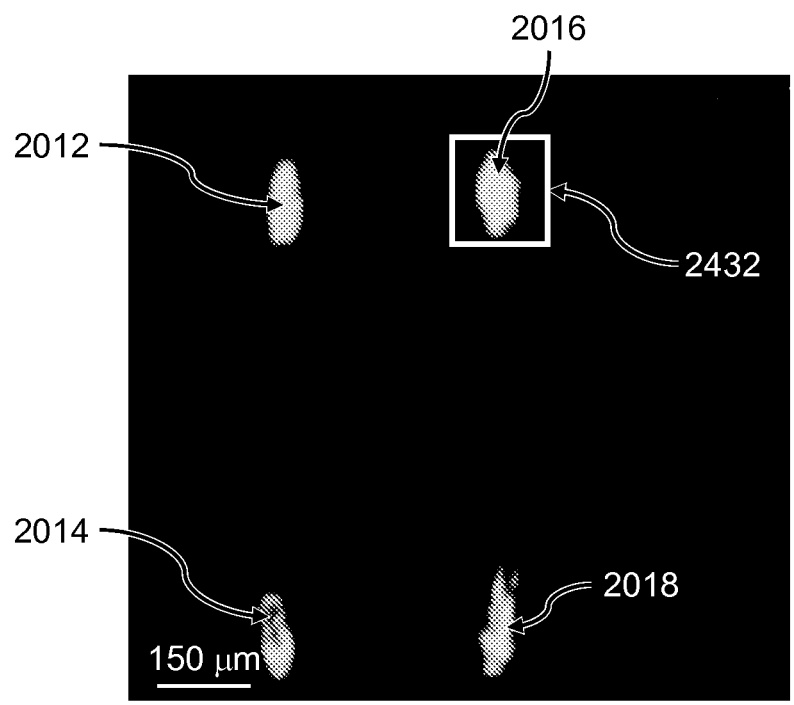
FIG. 24 is a 4× TRITC fluorescence micrograph of patterns of DOTAP multilayers printed directly onto glass using a microarrayer.
Figure 25:
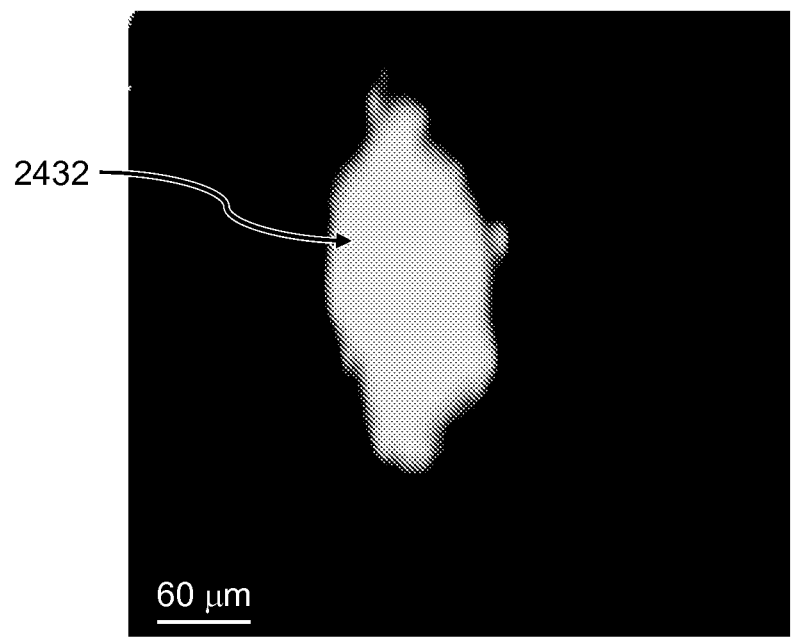
FIG. 25 is an image showing the digital zoom of the spot in indicated with the white square in FIG. 17.
Figure 26:
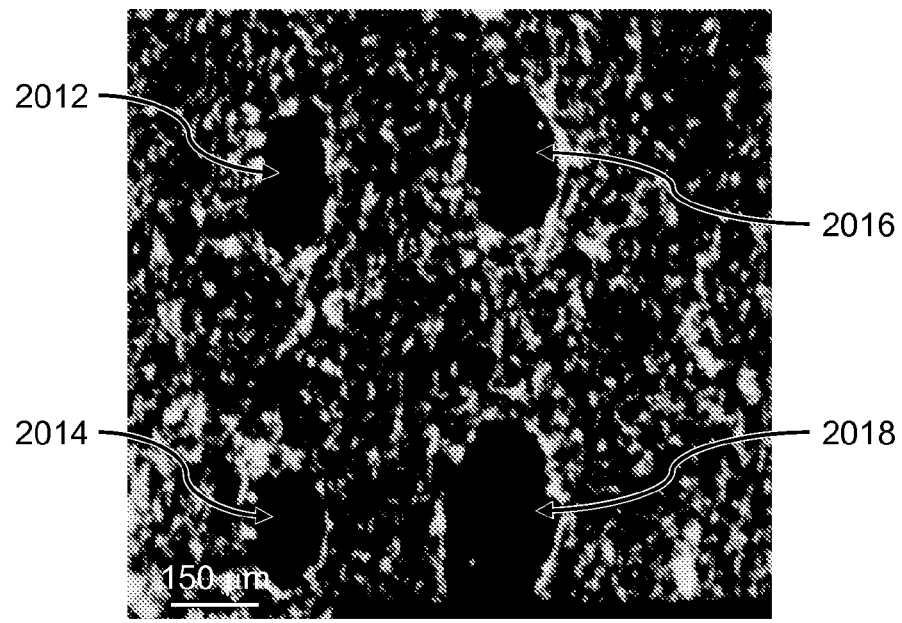
FIG. 26 is a 4× merged fluorescence micrograph of FITC and TRITC images of spots in FIG. 14.
Figure 27:
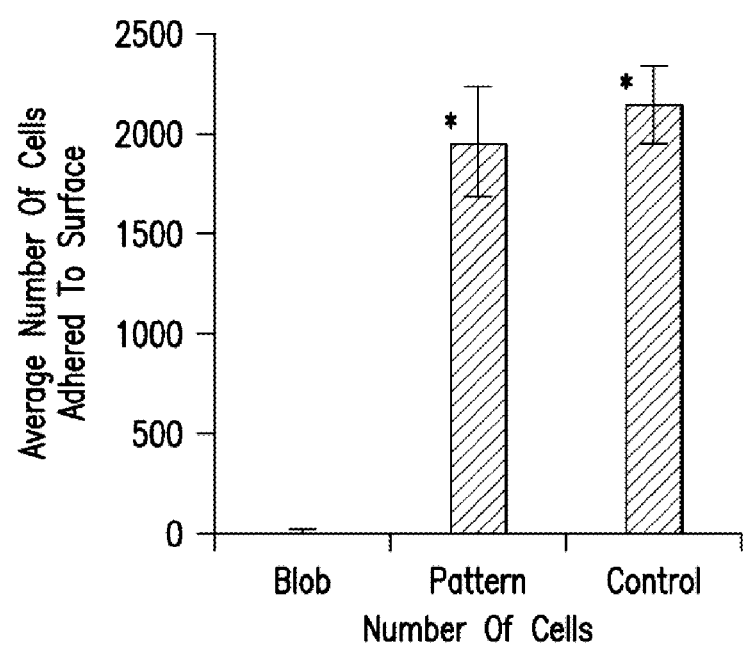
FIG. 27 is a graph showing that cells binding to both the patterned area and the non-patterned area efficiently but not to the areas with the blobs.

FIGS. 20, 21, 22, 23, 24, 25, 26 and 27 show how cells bind to and grow on patterned areas but not on the contiguous lipid multilayers (blobs). FIG. 20 is a 4× TRITC fluorescence micrograph of patterns of DOTAP stamped spots 2012, 2014, 2016 and 2018 printed onto glass 2042 using a 5 μm well stamp. FIG. 20 includes a region 2052 enclosed in white box. FIG. 21 presents the digital zoom of region 2052 of FIG. 20 showing greater detail of stamped spot 2016. FIG. 22 is 4× merged fluorescence micrograph of FITC and TRITC images of stamped spots 2012, 2014, 2016 and 2018. HeLa cells seeded on patterns adhere and grow. FIG. 22 includes a region 2232 enclosed in a white box. FIG. 23 is a 10× merged fluorescence micrograph of FITC and TRITC images of region 2232 of FIG. 22 show greater detail of stamped spot 2014. FIG. 24 is a 4× TRITC fluorescence micrograph of patterns of DOTAP stamped spots 2012, 2014, 2016 and 2018 printed directly onto glass using a microarrayer. FIG. 24 includes a region 2432 enclosed in a white box. FIG. 25 is the digital zoom of region 2432 of FIG. 24 that shows greater details of spot 2016. FIG. 26 is a 4× merged fluorescence micrograph of FITC and TRITC images of spots 2012, 2014, 2016, and 2018 that HeLa cells seeded on. Blobs break off into the media and cells do not grow at areas where blobs were. FIG. 27 is a graph showing that cells binding to both the patterned area and the non-patterned area efficiently but not to the areas with the blobs. All living cells labeled with green Syto 9 cell stain. Lipids doped with rhodamine-PE. Cell numbers obtained from counting all the cells on 80 patterned areas in each well.

The lipids without drugs were printed on glass and the heights measured with an AFM as shown in FIGS. 15, 16, 17, 18 and 19. The printed patterns are spaced out enough to allow for cellular adhesions to form before the lipids spread. Large blobs without these spaces do not allow cells to grow on them and allow for lipid and drug uptake (FIGS. 20, 21, 22, 23, 24, 25, 26 and 27). NIH 3T3 cells plated on the patterns adhered similarly to the control surface without any lipids.

Example 4

Figure 28:
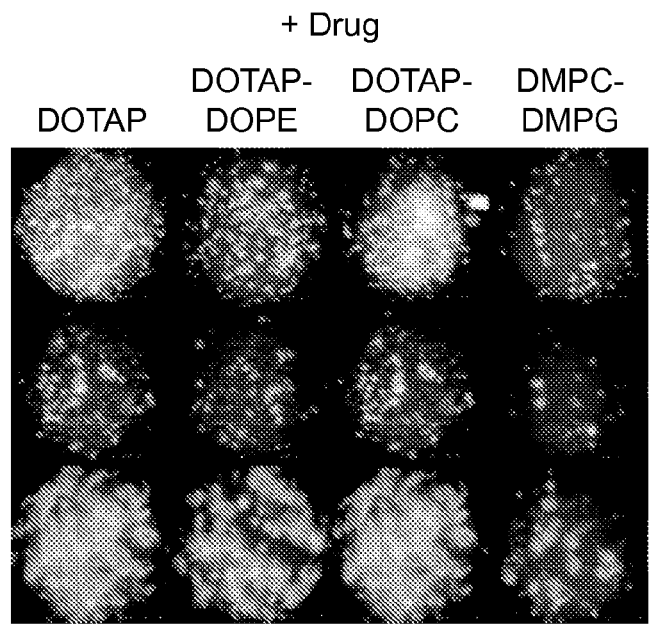
FIG. 28 is an image of cells cultured on the printed liposomes without the drug (docetaxel) and cultured for 79 hrs.
Figure 29:
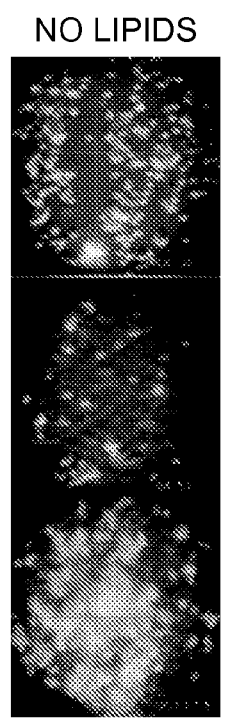
FIG. 29 is an image of cells on an area away from the patterns but in the same dish used as a negative control.

The effect of liposomal composition on the efficacy of docetaxel on HeLa cells is shown in FIGS. 28, 29, 31 and 32. In FIG. 28, cells are cultured on the printed liposomes without the drug (docetaxel) and cultured for 79 hours. FIG. 29 shows cells on an area away from the patterns but in the same dish used as a negative control.

Figure 30:
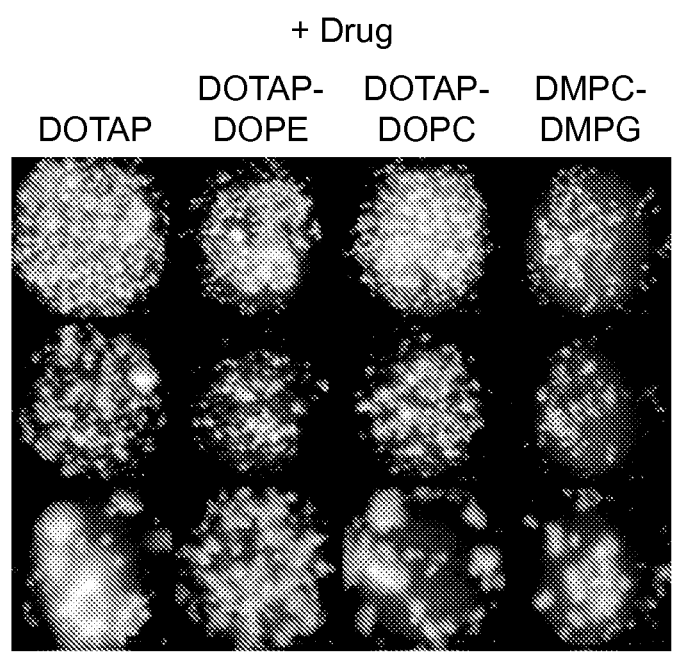
FIG. 30 is an image of cells cultured on the printed liposomes with the drug (docetaxel)) encapsulated and culture for 79 hours.
Figure 31:
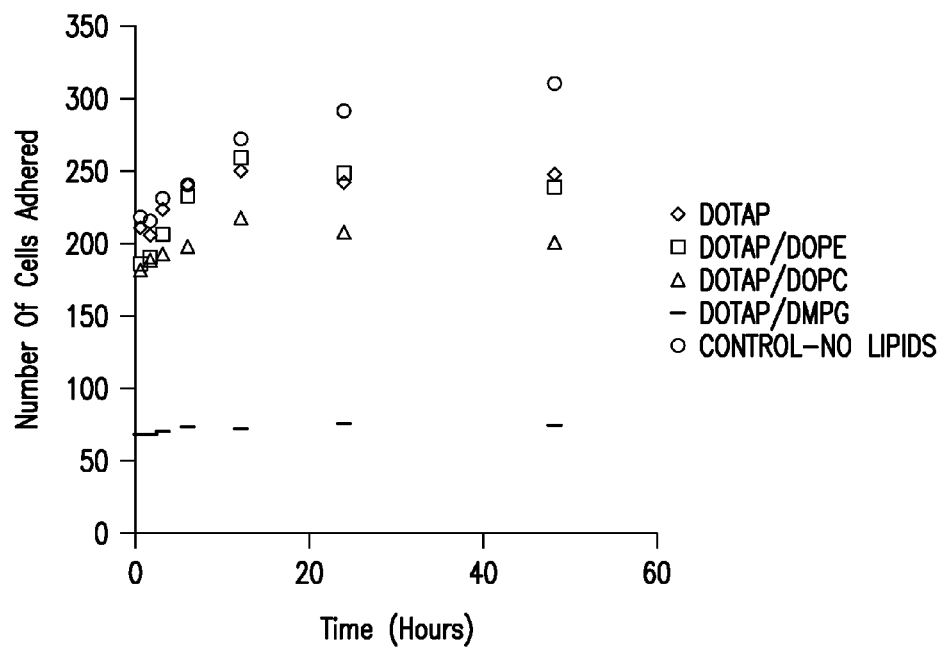
FIG. 31 is a graph showing the adhesion of cells on control lipids (without drug) over 79 hrs.
Figure 32:
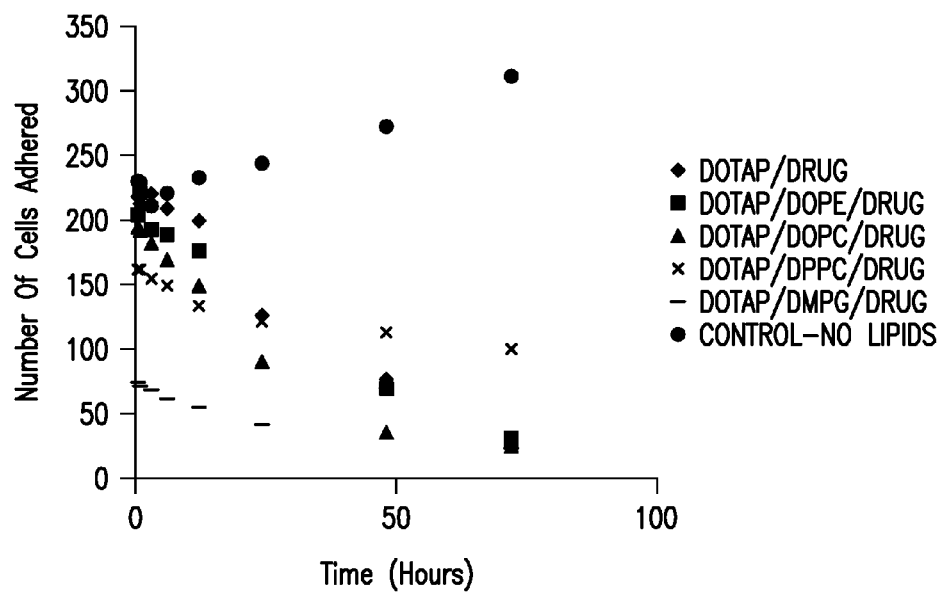
FIG. 32 is a graph showing the adhesion of cells on drug encapsulated lipids over 79 hours as a test for liposomal dependent efficacy of the drug (docetaxel).

FIG. 30 shows drug encapsulated in the first row of pictures in FIGS. 28 and 29 with stamped timepoint 0 represent the cells after 30 minutes in culture during which the microscope was being equilibrated. FIG. 31 is a graph showing adhesion of cells on control lipids (without drug) over 79 hours. FIG. 32 is a graph showing adhesion of cells on drug encapsulated lipids over 79 hours as a test for liposomal dependent efficacy of the drug (docetaxel).

Immersion of the samples under water was done under a nitrogen atmosphere as the only alternative short of in situ printing under water.[38] This was done without destruction of the liposome carrier array for the drugs.

Example 5

Figure 33:
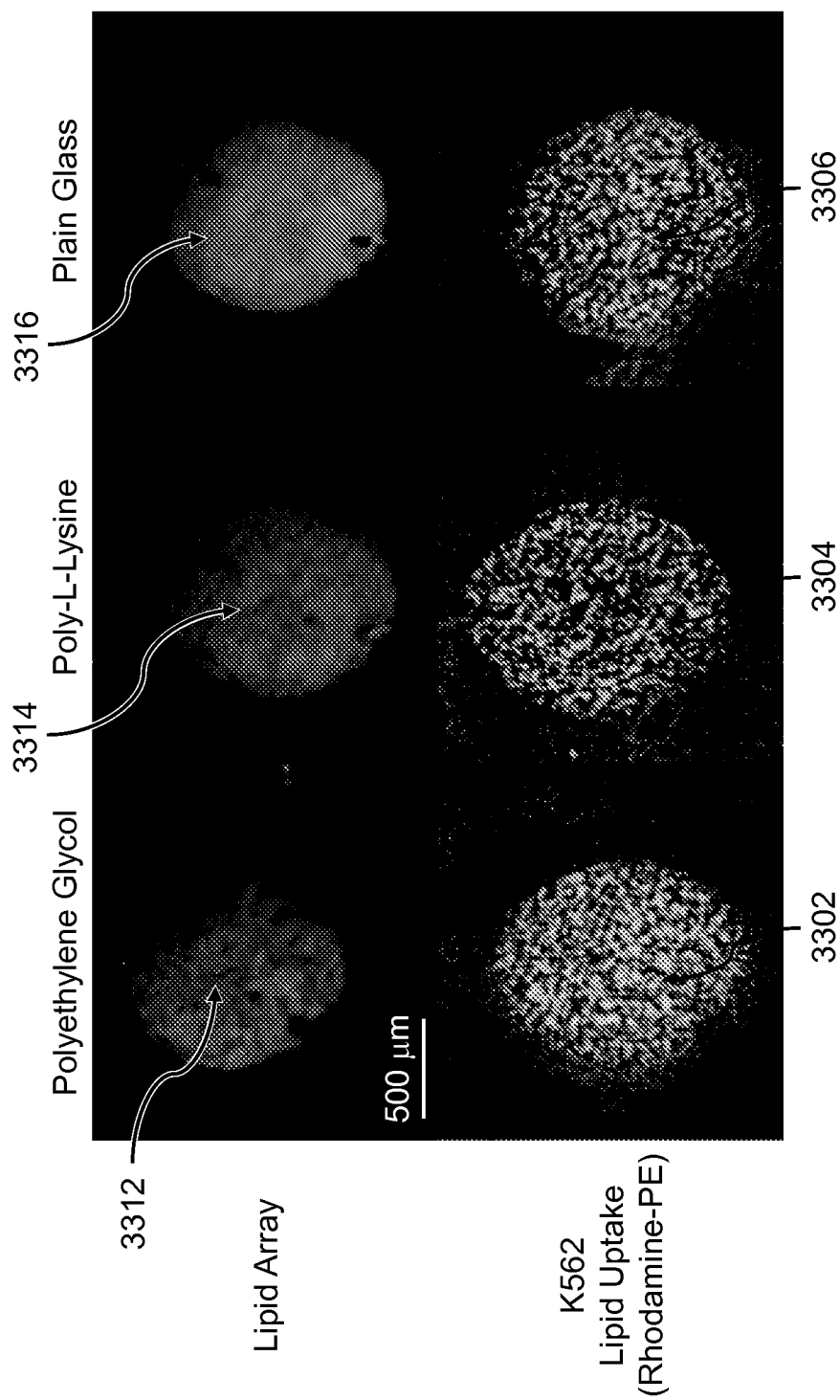
FIG. 33 is a merged image showing the adhesion of bright field and rhodamine of K562 lipid array on (A) Poly Ethylene Glycol, (B) Poly-L Lysine and (C) plain glass.

Cationic liposomes printed using the technique above can be used to localize suspension cells in order to screen them in a high throughput manner. The myeloid leukemic cell model K562 are suspension cells, and so far liposome microarray technology has only been demonstrated on adherent cells. However, FIG. 33 shows that K562 suspension cells can adhere to Poly Ethylene Glycol (PEG) (see image 3302), Poly-L-Lysine (PLL) (see image 3304), and plain glass liposome microarrays in culture (see image 3306). When seeded at 0.5 million cells/mL (250,000 cells/ 22 mm$^2$) K562 cells were found to adhere to all three substrates evaluated to differing degrees: plain glass, Polyethylene Glycol (PEG), and Poly-L-Lysine (PLL). Images 3312, 3314 and 3316 show the liposome microarrays on which the K562 cells of images 3302, 3304 and 3306, respectively, were deposited.

Example 6

Figure 34:
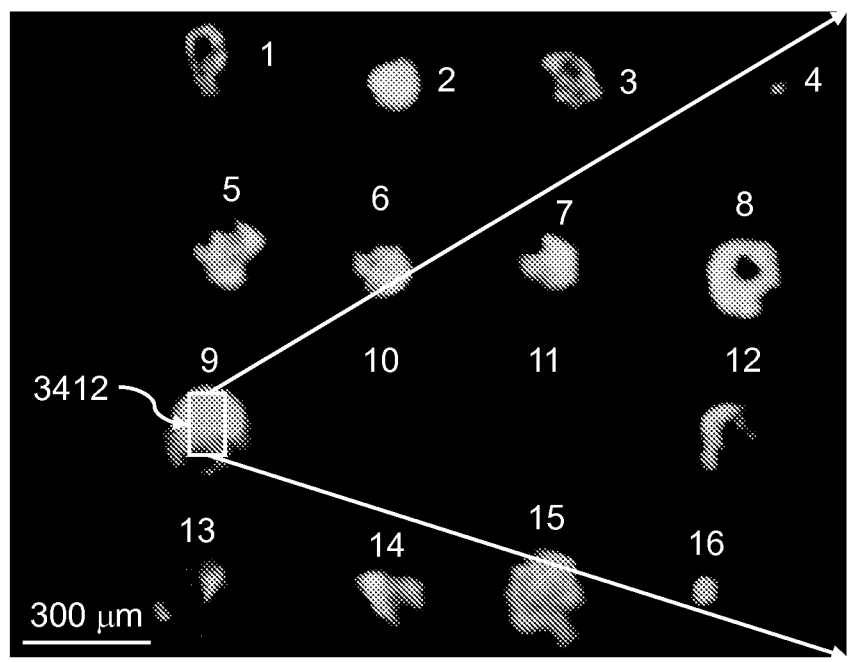
FIG. 34 is a fluorescence micrograph of 4*4 array of lipid formulations on glass in air.
Figure 35:
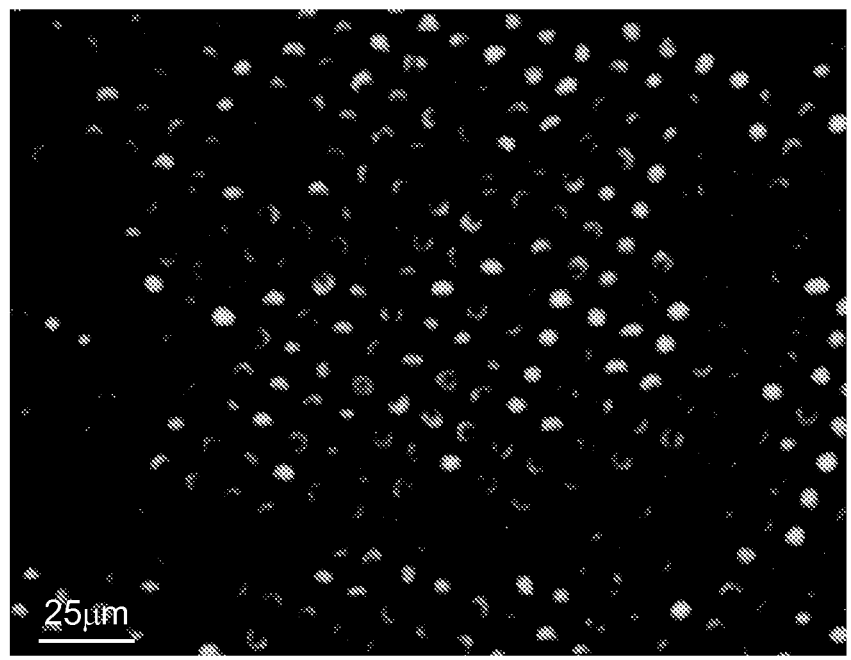
FIG. 35 is a 40× image of the region indicated by a white box in FIG. 29.
Figure 36:
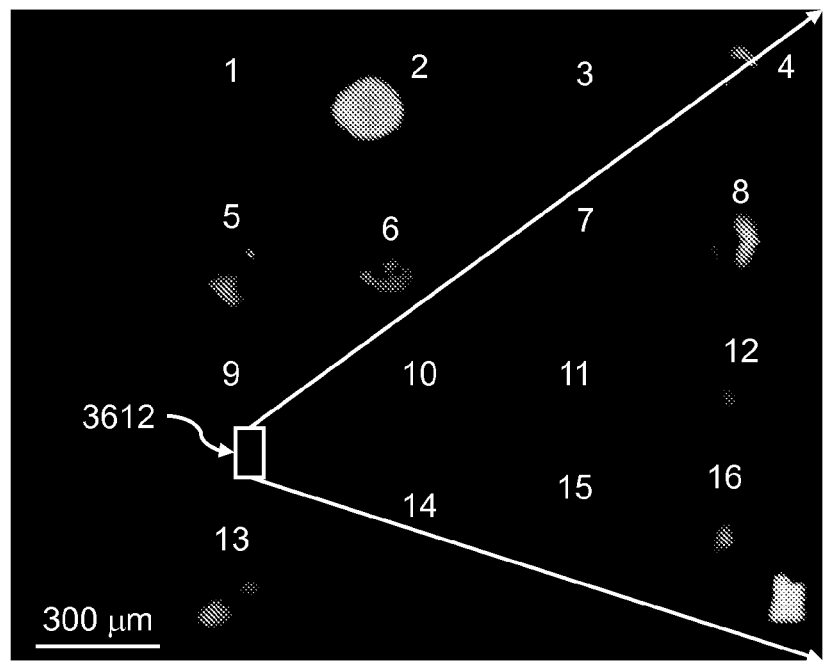
FIG. 36 is an image of arrays stamped onto glass slide and immersed underwater in a nitrogen atmosphere.
Figure 37:
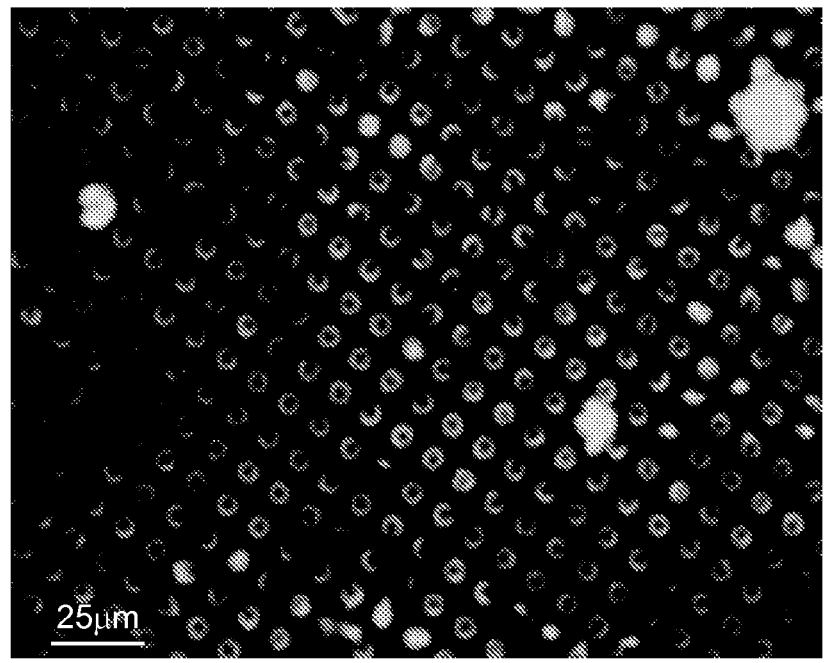
FIG. 37 is a 40× image of the region indicated by a white box in FIG. 36.
Figure 38:
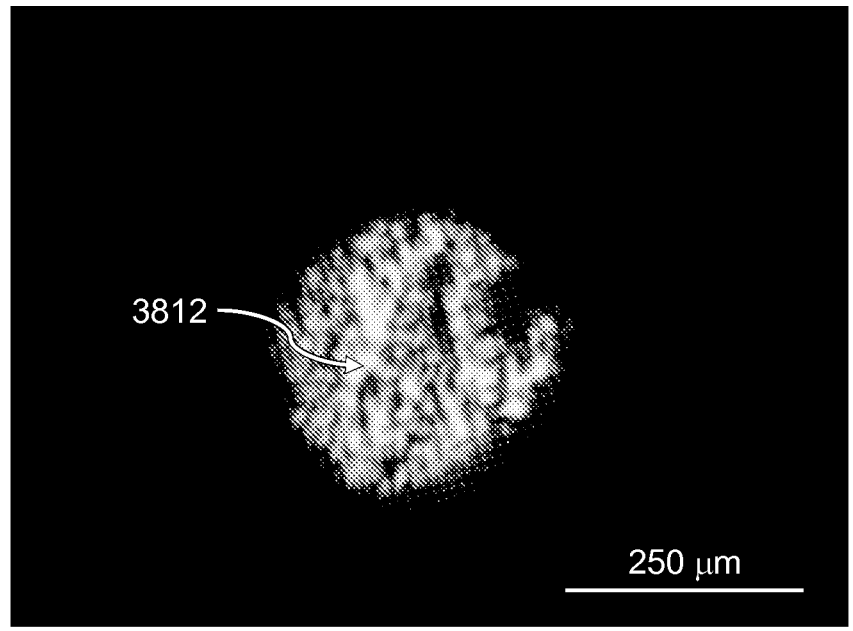
FIG. 38 is an image of spots patterned using scalable lipid multilayer stamping and printed the second time from the same stamp.
Figure 39:
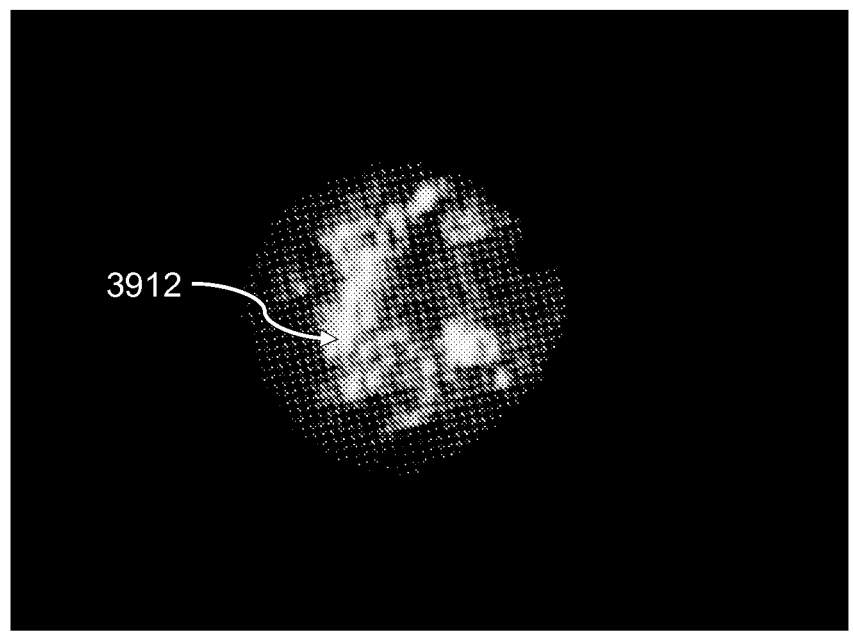
FIG. 39 is an image of spots patterned using scalable lipid multilayer stamping and printed the fourth time from the same stamp.
Figure 40:
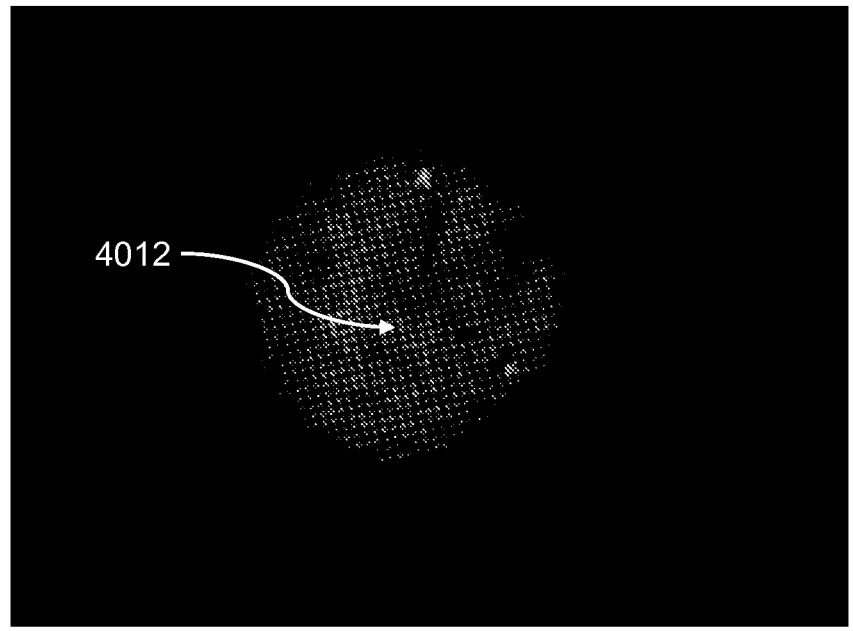
FIG. 40 is an image of spots patterned using scalable lipid multilayer stamping and printed the sixth time from the same stamp.
Figure 41:
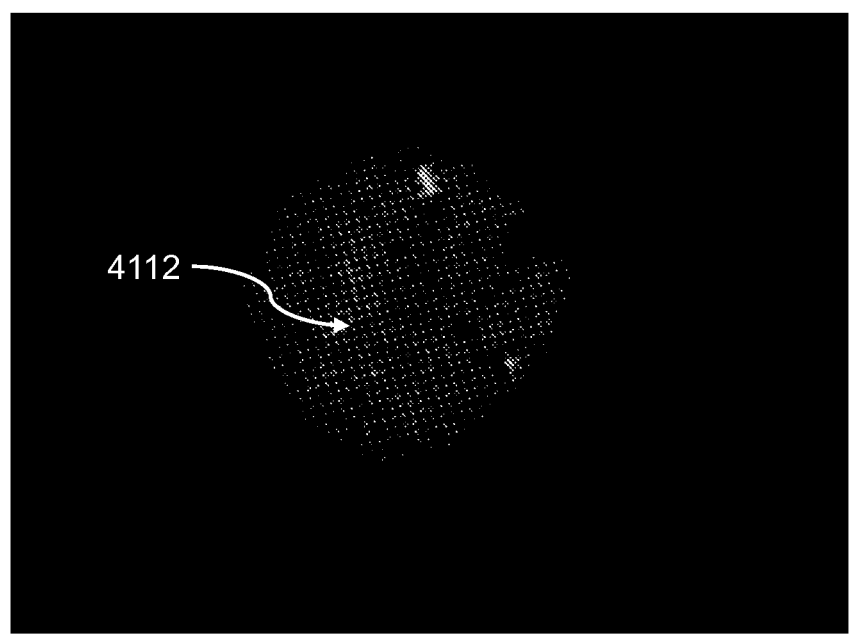
FIG. 41 is an image of spots patterned using scalable lipid multilayer stamping and printed the eighth time from the same stamp.

Patterns are immmersible under water in a nitrogen atmosphere, as depicted in FIGS. 34, 35, 36 and 37. FIG. 34 is a fluorescence micrograph of 4×4 array of lipid formulations 1 through 16 on glass in air. Each spot is numbered, and the compositions are: [1] DOTAP only, [2] DOTAP+Valinomycin (1:1), [3] DOTAP+Valinomycin (2:1), [4] DOTAP+ Valinomycin (4:1), [5]—DOTAP+Valinomycin (8:1), [6] DOTAP/DOPE(30:70)+Valinomycin (1:1), [7] DOTAP/ DOPE(30:70)+Valinomycin (2:1), [8] DOTAP/DOPE (30: 70)+Valinomycin (4:1), [9] DOTAP/DOPE (30:70)+Valinomycin (8:1), [10] DOTAP/Cholesterol (20 mol %)+Valinomycin (1:1), [11] DOTAP/Cholesterol(20 mol %)+Valinomycin (2:1), [12] DOTAP/Cholesterol(20 mol %)+Valinomycin (4:1), [13] DOTAP/Cholesterol (20 mol %)+Valinomycin (8:1), [14] DOTAP/DOPE(30:70)/Cholesterol(20 mol %)+Valinomycin (1:1), [15] DOTAP/DOPE (30:70)/Cholesterol(20 mol %)+Valinomycin (2:1), [16] DOTAP/DOPE(30:70). FIG. 34 includes a region 3412 enclosed in a white box. FIG. 35 is a 40× image of region 3412 of FIG. 34. FIG. 36 shows arrays 1 through 16 stamped onto glass slide and immersed under water in a nitrogen atmosphere. FIG. 36 includes a region 3612 enclosed in a white box. FIG. 37 is a 40× image of region 3612 of FIG. 36.

Example 7

Figure 42:
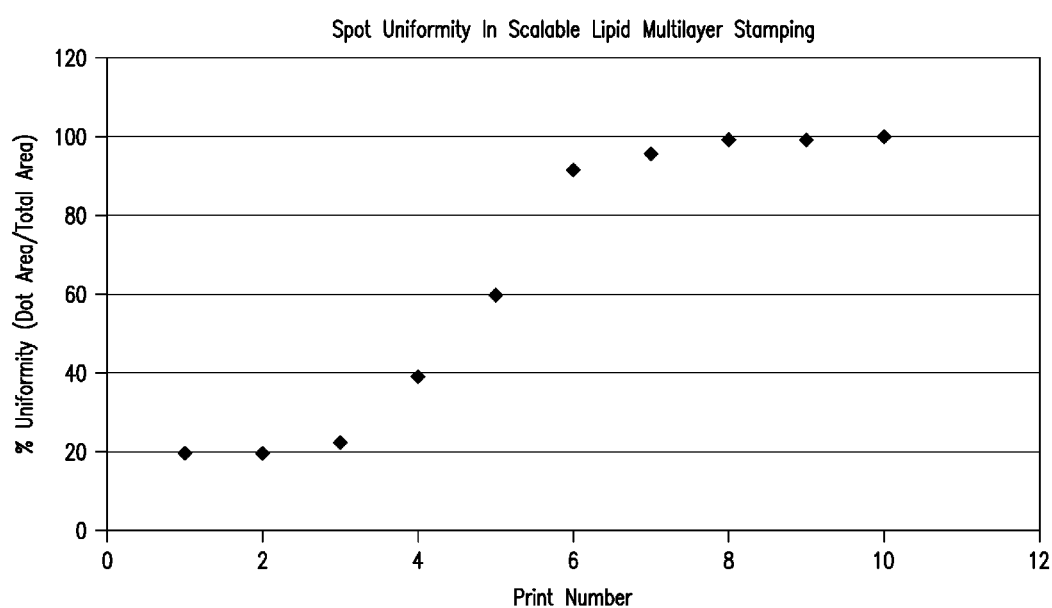
FIG. 42 is a graph showing spot uniformity in scalable lipid multilayer stamping.

FIGS. 38, 39, 40 and 41 are images of spots of print number 2 (spot 3812), 4 (spot 3912), 6 (spot 4012) and 8 (spot 4112) patterned using scalable lipid multilayer stamping, and printed several times from the same stamp. Spots become more uniform as excess ink is removed, as shown in the graph in FIG. 42.

Example 8

Figure 43:
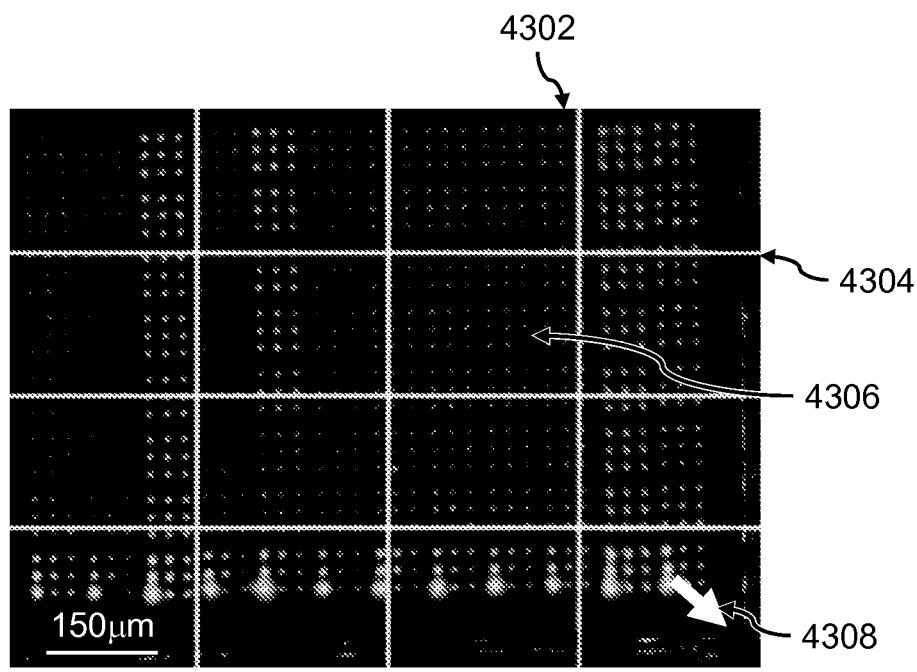
FIG. 43 is a merged image of phase contrast and fluorescent images of a rhodamine-labeled phospholipid DPN pattern before cell culture for a sample.
Figure 44:
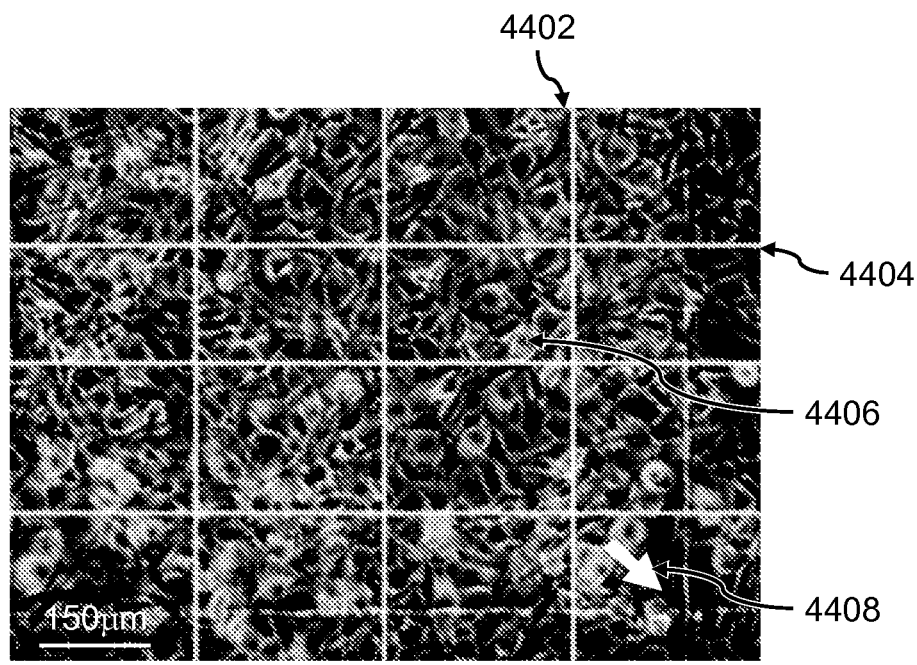
FIG. 44 is an image of cells after incubation over the pattern in FIG. 43 for 18 hours for the sample of FIG. 43.
Figure 45:
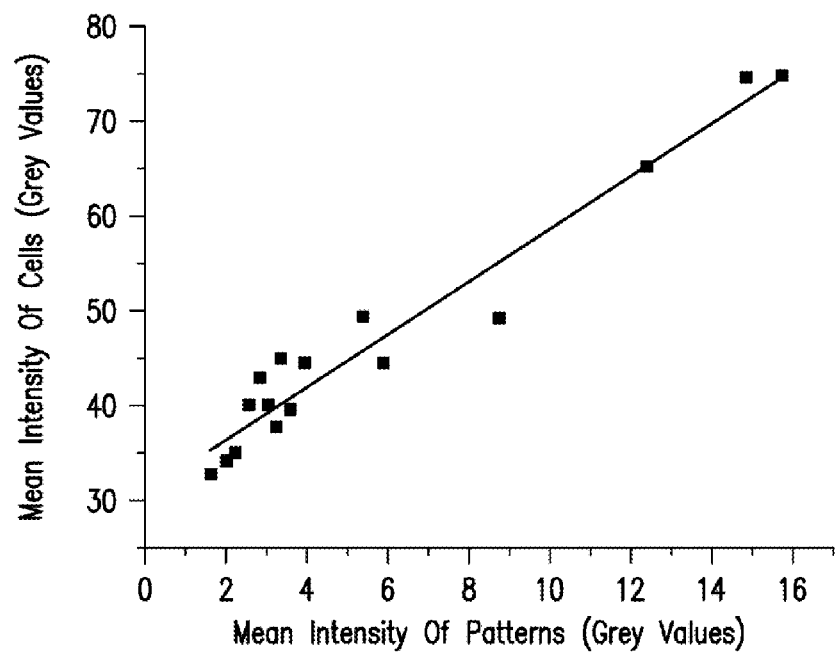
FIG. 45 is a graph showing an analysis of the correlation of intensity of spots with the average intensity of the cells for the sample of FIG. 43.
Figure 46:
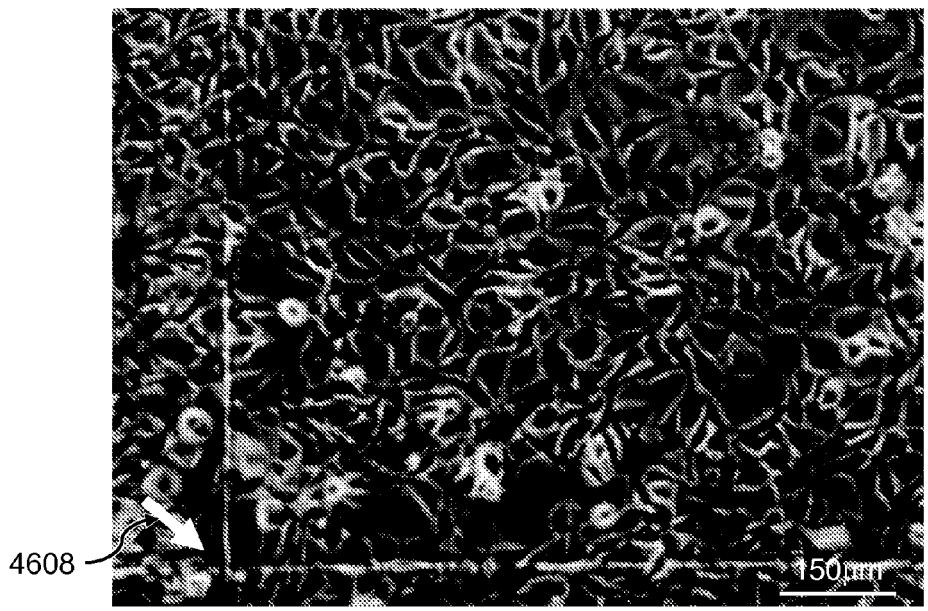
FIG. 46 is an imaging showing cells residing in a region immediately to the right of the region shown FIG. 44.

To demonstrate and quantify lipid uptake by the cells, NIH 3T3 cells are cultured over a rhodamine-doped lipid multilayer pattern for 24 hours. FIGS. 43, 44, 45 and 46 show the uptake of DOPE-rhodamine-labeled DOTAP by NIH 3T3 cells. FIGS. 43, 44 and 46 are all images from the same sample. FIG. 43 is a merged image of phase contrast and fluorescent images of a rhodamine-labeled phospholipid DPN pattern (array) before cell culture. FIG. 44 is an image of cells after incubation over the pattern in FIG. 43 for 18 hours. Fluorescence intensity is used as the indicator of the amount of lipid taken up by the cells. A higher fluorescence in cells indicates higher uptake of lipids. Grid lines 4302 and 4304 in FIG. 43 divide the image of FIG. 43 into equal areas 4306. Also shown in FIG. 43 is an arrow 4308. Grid lines 4402 and 4404 in FIG. 44 divide the images of FIGS. 44 into equal areas 4406. Also shown in FIG. 44 is an arrow 4408. Cells were analyzed and compared for fluorescence intensity before and after cell incubation on the patterns. This division provided the highest correlation of the fluorescent intensities of the patterns with those of the cells, suggesting that this area is the average distance the cells migrated during the experiment. FIG. 45 is a graph showing an analysis of the correlation of intensity of dots with the average intensity of the cells. Images are divided into equal areas 4306 of FIG. 43 and equal areas of FIG. 44 for determination of the localization of the cells to their sources of lipids. The linearity of this relation indicates the possibility of obtaining dose-response curves from a single area of an array. The cells over the dots with high fluorescence intensity took up the most lipids and showed the highest intensity. FIG. 46 shows that cells residing in a region immediately to the right of the region shown in FIG. 44 do not fluoresce. Also shown in FIG. 46 is an arrow 4608. The contrast of images has been adjusted in the look-up tables of the NIKON NIS software for viewing purposes only. Arrows 4308, 4408 and 4608 point to common alignment marks that are scratched on the glass coverslip for the sample.

Example 9

FIG. 46 shows an area directly next to that shown in of FIG. 44, indicating that cells next to the spot do not take up lipids.

Figure 47:
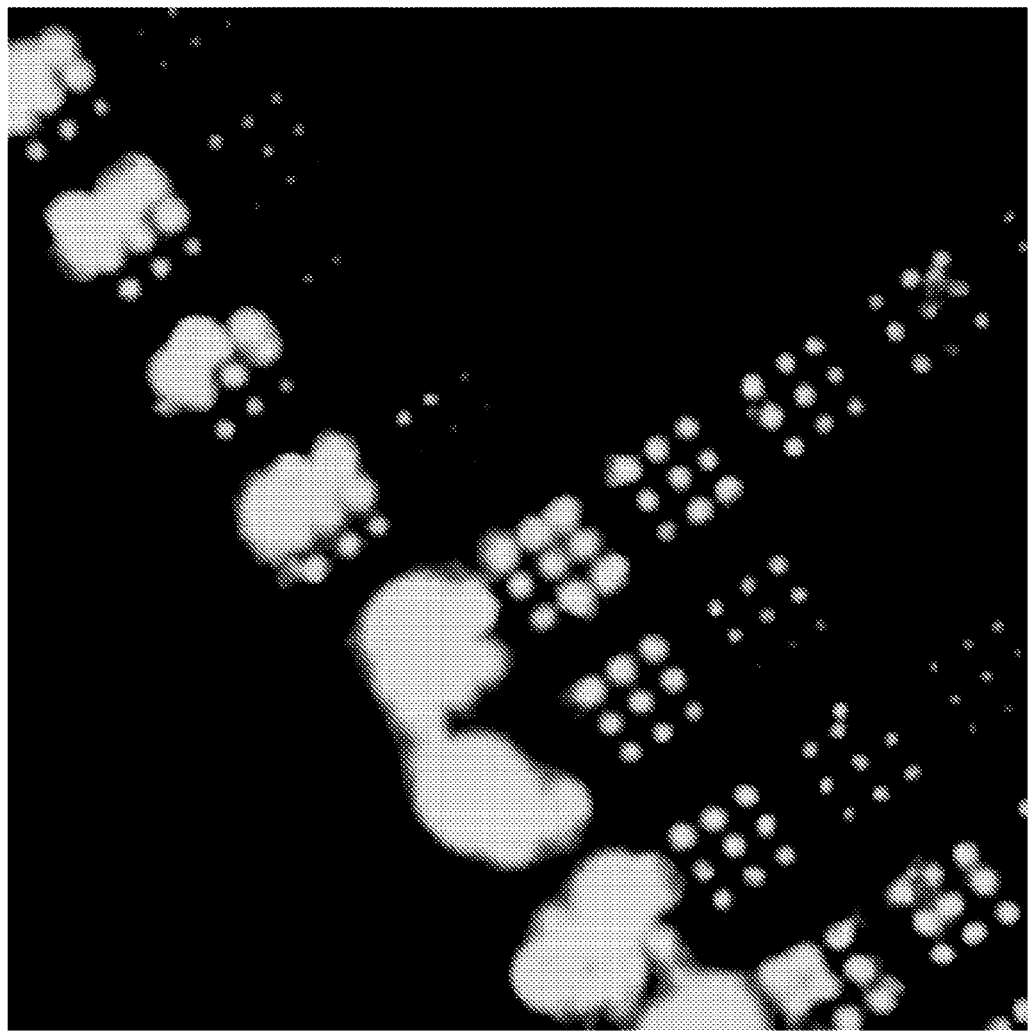
FIG. 47 is a fluorescence micrograph of a lipid multilayer microarray. Live cell imaging revealed cell adhesion to the surface and uptake of the lipids from the array.

FIG. 47 shows a fluorescence micrograph of a lipid multilayer microarray. Live cell imaging revealed cell adhesion to the surface and uptake of the lipids from the array.

Figure 48:
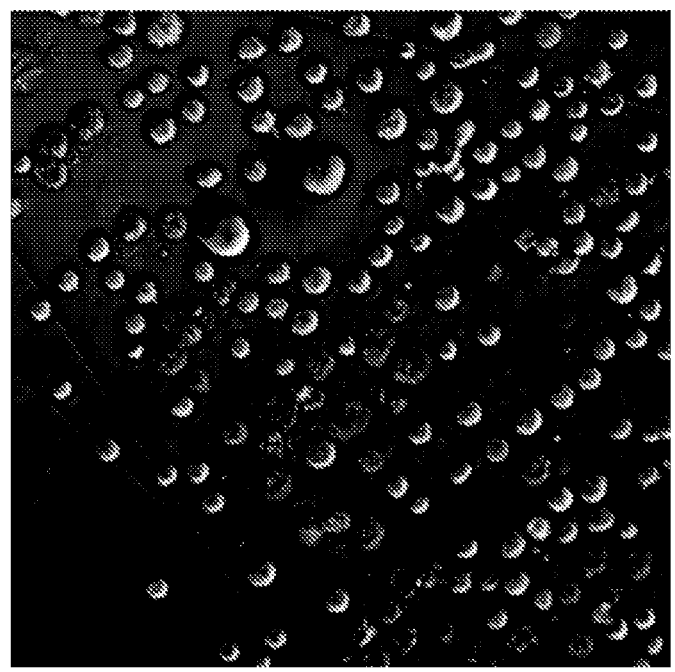
FIG. 48 is a brightfield micrograph of cells cultured over the lipid multilayer microarray.

FIG. 48 shows a brightfield micrograph of cells cultured over the lipid multilayer microarray.

Figure 49:
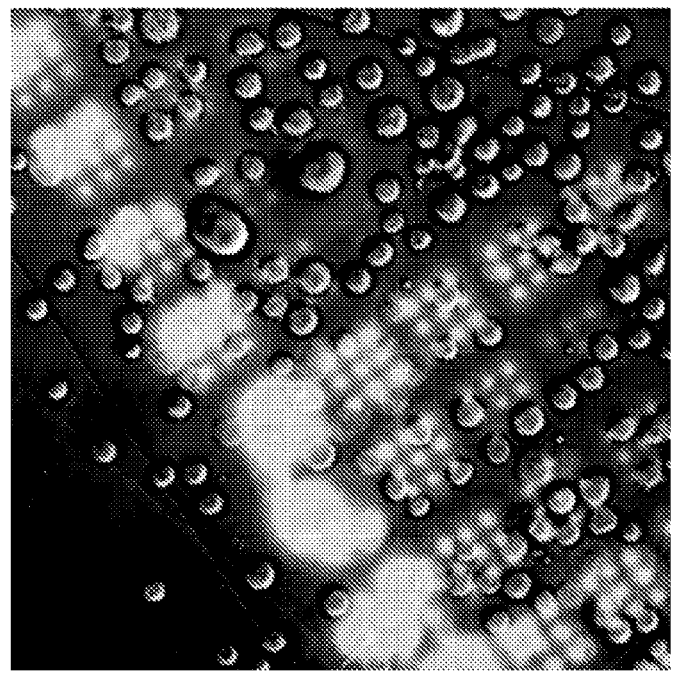
FIG. 49 is an overlay of FIG. 47 and FIG. 48.

FIG. 49 shows is an overlay of FIG. 47 and FIG. 48.

Figure 50:
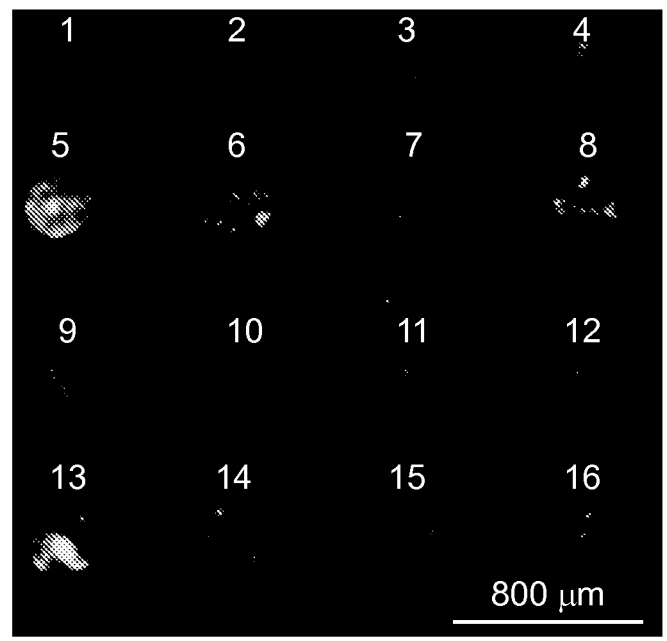
FIG. 50 is a fluorescence micrograph of an array of 16 different lipid mixtures, labeled green with a fluorescently labeled lipid.

FIG. 50 shows a fluorescence micrograph of an array of 16 different lipid mixtures, labeled green with a fluorescently labeled lipid.

Example 10

Figure 51:
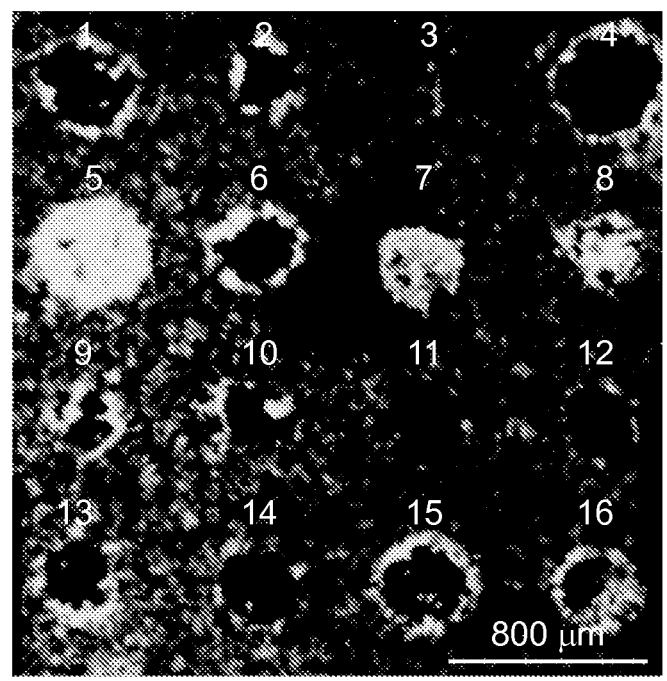
FIG. 51 is a fluorescence micrograph of cells after culture on the array and staining.
Figure 52:
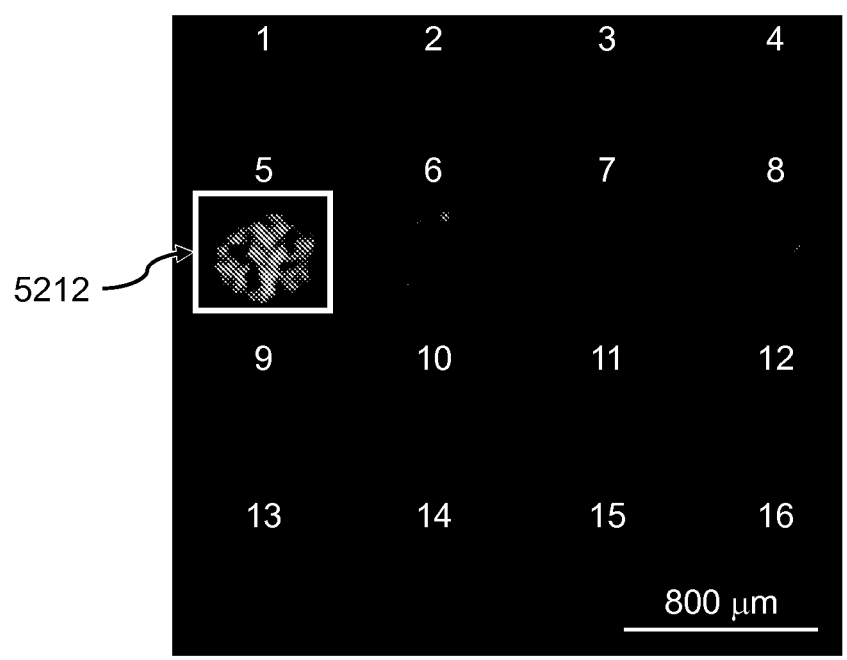
FIG. 52 is an image of the results of experiment where 16 different liposomal drug formulations arrayed onto a PDSM stamp and arrayed onto a glass surface.
Figure 53:
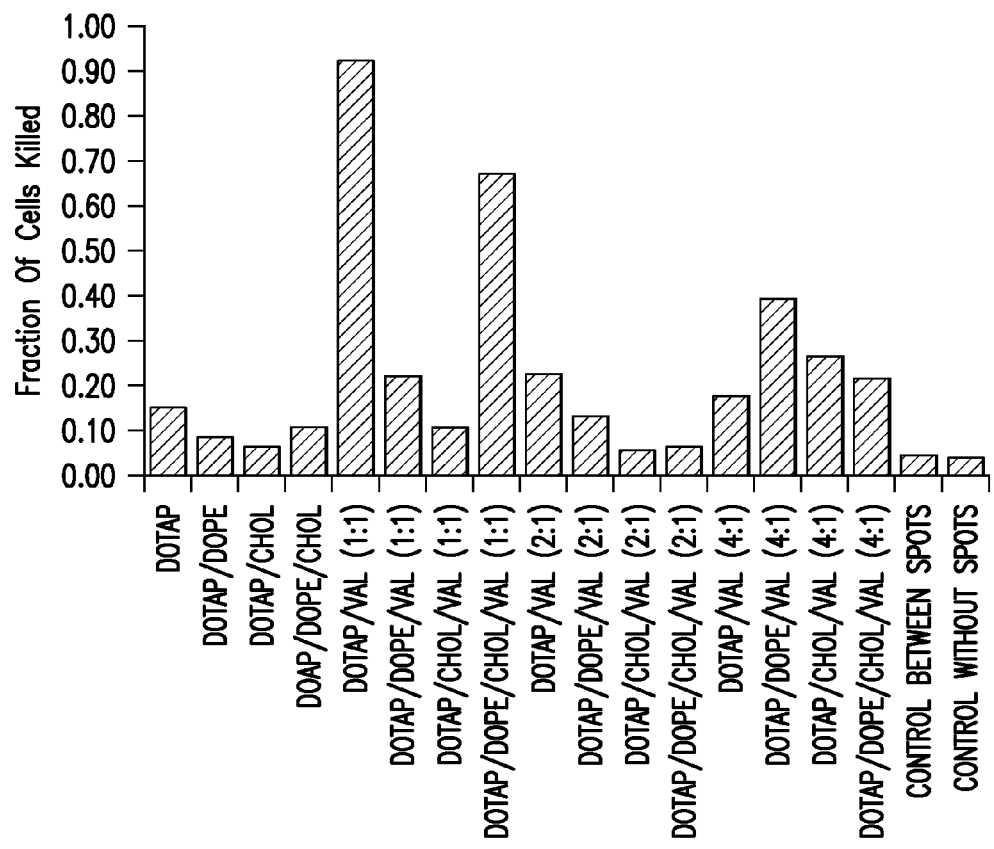
FIG. 53 is a graph showing the fraction of cells killed over each drug pattern area for the efficacy assay of FIG. 52.
Figure 54:
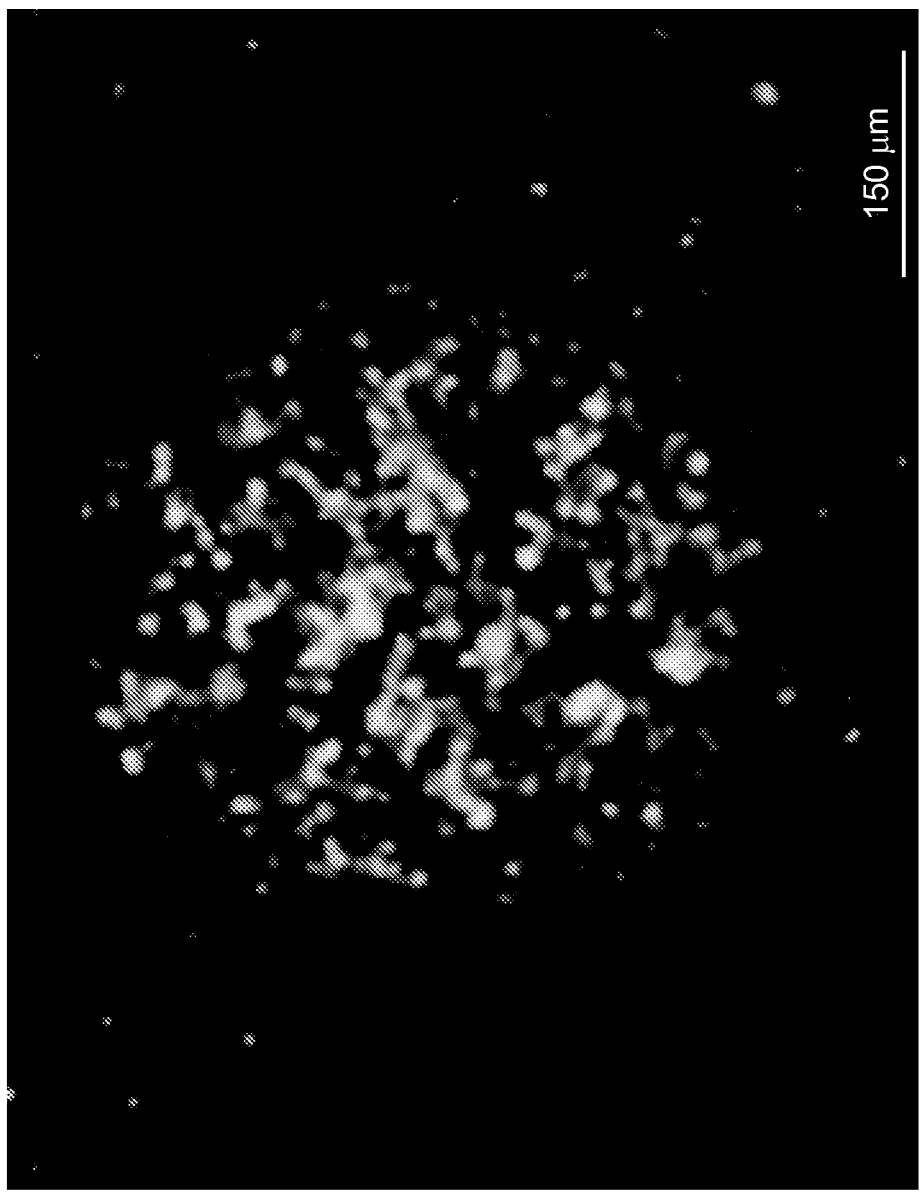
FIG. 54 is an enlarged view of a boxed region of FIG. 52.

Sixteen different liposomal drug formulations were array onto a PDMS stamp and arrayed onto a glass surface as shown in FIG. 50. The sixteen different formulations were: [1] DOTAP only, [2] DOTAP+Valinomycin (1:1), [3] DOTAP+Valinomycin (2:1), [4] DOTAP+Valinomycin (4:1), [5]—DOTAP+Valinomycin (8:1), [6] DOTAP/DOPE (30:70)+Valinomycin (1:1), [7] DOTAP/DOPE(30:70)+Valinomycin (2:1), [8] DOTAP/DOPE (30:70)+Valinomycin (4:1), [9] DOTAP/DOPE (30:70)+Valinomycin (8:1), [10] DOTAP/Cholesterol (20 mol %)+Valinomycin (1:1), [11] DOTAP/Cholesterol(20 mol %)+Valinomycin (2:1), [12] DOTAP/Cholesterol(20 mol %)+Valinomycin (4:1), [13] DOTAP/Cholesterol (20 mol %)+Valinomycin (8:1), [14] DOTAP/DOPE(30:70)/Cholesterol(20 mol %)+Valinomycin (1:1), [15] DOTAP/DOPE(30:70)/Cholesterol(20 mol %)+Valinomycin (2:1), [16] DOTAP/DOPE(30:70), indicated by numbers 1, 2, 3, 4, 5, 6, 7, 8, 9, 10, 11, 12, 13, 14, 15 and 16 respectively in FIGS. 51, 52 and 53. FIG. 51 shows cells cultured on each of the sixteen different formulations. FIG. 52 is an image of the results of the experiment where the 16 different liposomal drug formulations arrayed onto a PDSM stamp and arrayed onto a glass surface. Boxed region 5212 of FIG. 52 shows the results for formulation 5. FIG. 53 is a graph showing the fraction of cells killed over each drug pattern area for the efficacy assay of FIG. 50 as well as for control regions between the sixteen spots and for control regions without spots. FIG. 54 is an enlarged view of boxed region 5212.

All documents, patents, journal articles and other materials cited in the present application are incorporated herein by reference.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

REFERENCES

The following references are referred to above and are incorporated herein by reference:

1. Barenholz, Y., Gibbes, D., Litman, B. J., Goll, J., Thompson, T. E., and Carlson, F. D., "A simple method for the preparation of homogeneous phospholipid vesicles," *Biochemistry* 16, 2806-10 (1977).
2. Szokam F., and Papahadjopoulos, D., "Comparative properties and methods of preparation of lipid vesicles (liposomes)," *Annu. Rev. Biophys. Bio* 9, 467-508 (1980).
3. Gustafsson, J., Arvidson, G., Karlsson, G., and Almgren, M. "Complexes between cationic liposomes and DNA visualized by Cryo-Tem," *BBA-Biomembranes* 1235, 305-12 (1995).
4. Kwon, C. H., Wheeldon, I., Kachouie, N. N., Lee, S. H., Bae, H., Sant, S., Fukuda, J., Kang, J. W., Khademhosseini, A., "Drug-eluting microarrays for cell-based screening of chemical-induced apoptosis," *Anal. Chem.* 83, 4118-25 (2011).
5. Malam, Y., Loizidou, M., and Seifalian, A. M., "Liposomes and nanoparticles: nanosized vehicles for drug delivery in cancer," *Trends Pharmacol. Sci.* 30, 592-99 (2009).
6. Porter, C. J. H., Trevaskis, N. L., and Charman, W. N., "Lipids and lipid-based formulations:optimizing the oral delivery of lipophilic drugs," *Nat. Rev. Drug Discov.* 6, 231-48 (2007).
7. Torchilin, V. P., "Micellar nanocarriers: pharmaceutical perspectives," *Pharm. Res.* 24, 1-16 (2007).
8. Koren, E., and Torchilin, V. P., "Drug carriers for vascular drug delivery," *IUBMB Life* 63, 586-95 (2011).
9. Gregoriadis, G., "Engineering liposomes for drug delivery: progress and problems," *Trends in Biotechnology* 13, 527-37 (1995).
10. Kusi-Appiah, A. E., Vafai, N., Cranfill, P. J., Davidson, M. W., and Lenhert, S., "Lipid multilayer microarrays for in vitro lipomosomal drug delivery and screening," *Biomaterials* 33, 4187-94 (2012).
11. Majd, S, and Mayer, M., "Hydrogel stamping of arrays of supported lipid bilayers with various lipid compositions for the screening of drug-membrane and protein-membrane interactions,"*Angew. Chem. Int. Ed.* 44, 6697-6700 (2005).
12. Moran-Mirabal, J. M., Edel, J. B., Meyer, G. D., Throckmorton, D., Singh, A. K., and Craighead, H. G., "Micrometer-sized supported lipid bilayer arrays for bacterial toxin binding studies through total internal reflection fluorescence microscopy," *Biophys. J.* 89, 296-305 (2005).
13. Deng, Y., Wang, Y., Holtz, B. Li, J., Traaseth, N., Veglia, G., Stottrup, B. J., Elde, R., Pei, D., Guo, A., and Zhu, X. Y., "Fluidic and air-stavle supported lipid bilayer and cell-mimicking microarrays," *J. Am. Chem. Soc.* 130, 6267-71 (2008).
14. Yamazaki, V., Sirenko, O., Schafer, R. J., Nguyen, L., Gutsmann, T., Brade, L., and Groves, J. T., "Cell membrane array fabrication and assay technology," *BMC Biotechnology* 2005, doi:10.1186/1472-6750-5-18 (2005).
15. Lenhert, S., Brinkmann, F., Laue, T., Walheim, S., Vannahme, C., Klinkhammer, S., Xu, M., Sekula, S., Mappes, T., Schimmel, T., and Fuchs, H., "Lipid multilayer gratings," *Nat. Nanotechnol.* 5, 275-79 (2010).
16. Lenhert, S., Sun, P., Wang, Y. H., Fuchs, H., and Mirkin, C. A., "Massively parallel dip-pen nanolithography of heterogeneous supported phospholipid multilayer patterns," *Small* 3, 71-75 (2007).
17. Sekula, S., Fuchs, J., Weg-Remers, S., Nagel, P., Schuppler, S., Fragala, J., Theilacker, N., Franzreb, M., Wingren, C., Ellmark, P., Borrebaeck, C. A. K., Mirkin, C. A., Fuchs, H., and Lenhert, S., "Multiplexed lipid dip-pen nanolithography on subcellular scales for the templating of functional proteins and cell culture," *Small* 4, 1785-93 (2008).
18. Nafday, O. A., and Lenhert, S. "High-throughput optical quality control of lipid multilayers fabricated by dip-pen nanolithography," *Nanotechnology* 22, doi:225301 (2011).
19. Perino-Gallice, L., Fragneto, G., Mennicker, U., Salditt, T., and Rieutord, F., "Dewetting of solid-supported multilamellar lipid layers," *Eur. Phys. J. E* 8, 275-82 (2002).
20. Mathieu, M. Schunk, D., Franzka, S., Mayer, C., and Hartmann, N., "Temporal stability of photothermally fabricated micropatterns in supported phospholipid multilayers," *J. Vac. Sci. Technol. A* 28, 953-57 (2010).
21. Perl, A., Reinhoudt, D. N., and Huskens, J., "Microcontact printing: limitations and achievements," *Adv. Mater.* 21, 2257-68 (2009).
22. Nafday, O. A., Lowry, T. W., and Lenhert, S., "Multifunctional lipid multilayer stamping," *Small* 8, 1021-28 (2012).

23. Heller, M. J., "DNA microarray technology: devices, systems, and applications," *Annu. Rev. Biomed. Eng.* 4, 129-53 (2002).

24. Howbrook, D. N., van der Valk, A. M., O'Shaughnessy, M. C., Sarker, D. K., Baker, S. C., and Lloyd, A. W., "Developments in microarray technologies," *Drug Discov. Today* 15, 648-51 (2003).

25. Eteshola, E., and Leckband, D., "Development and characterization of an ELISA assay in PDMS microfluidic channels," *Sens. Actuator B-Chem.* 72, 129-33 (2001).

26. Braunschweig, A. B., Huo, F. W., and Mirkin, C. A., "Molecular printing," *Nat. Chem.* 1, 353-58 (2009).

27. Salaita, K., Wang, Y. H., and Mirkin, C. A., "Applications of dip-pen nanolithography," *Nat. Nanotechnol.* 2, 145-55 (2007).

28. Ginger, D. S., Zhang, H., and Mirkin, C. A., "The evolution of dip-pen nanolithography," *Angew. Chem. Int. Ed.* 43, 30-45 (2004).

29. Piner, R. D., Zhu, J., Xu, F., Hong, S. H., and Mirkin, C. A., "Dip-pen" nanolithography," *Science* 283, 661-63

30. Salaita, K., Wang, Y. H., Fragala, J., Vega, R. A., Liu, C., Mirkin, C. A. "Massively parallel dip-pen nanolithography with 55000-pen two-dimensional arrays," *Angew. Chem. Int. Ed.* 45, 7220-23 (2006).

31. Zhang, M., Bullen, D., Chung, S. W., Hong, S., Ryu, K. S., Fanm Z. F., and Mirkin, C. A., and Liu, C., "A MEMS nanoplotter with high density parallel dip-pen nanolithography probe arrays," *Nanotechnology* 13, 212-17 (2002).

32. Xia, Y. N., and Whitesides, G. M., "Soft lithography," *Annu. Rev. Mater. Sci.* 28, 153-84 (1998).

33. Huo, F., Zheng, Z, Zheng, G, Giam, L., Zhang, H., and Mirkin, C. A., "Polymer pen lithography," *Science* 321 1658-60 (2008).

34. Kusi-Appiah, A., Vafai, N., Cranfill, P. J., Davidson, M. W. & Lenhert, S., "Lipid multilayer microarrays for in vitro liposomal drug delivery and screening," *Biomaterials* 33(16) 4187-94 (2012).

35. Jong, J. W., Smetana, A., and Stiles, P., "Multi-ink pattern generation by dip-pen nanolithography," *Scanning* 32, 24-29 (2010).

36. Chou, S. Y., Krauss, P. R., and Renstrom, P. J., "Imprint lithography with 25-nanometer resolution," *Science* 272, 85-87 (1996).

37. Torchilin, V. P., "Recent advances with liposomes as pharmaceutical carriers," *Nat. Rev. Drug Discov.* 4, 145-60 (2005).

38. Lenhert, S., Mirkin C. A., and Fuchs, H., "In situ lipid dip-pen nanolithography under water," *Scanning* 32, 15-23 (2010).

39. Mendez-Vilas, A., Jodar-Reyes, A. B., and Gonzalez-Martin, M. L., "Ultrasmall liquid droplets on solid surfaces: production, imaging, and relevance for current wetting research," *Small* 5, 1366-90 (2009).

40. Szymanski, P., Markowicz, M. & Mikiciuk-Olasik, E. Adaptation of High-Throughput Screening in Drug Discovery-Toxicological Screening Tests. International Journal of Molecular Sciences 13, 427-452 (2012).

What is claimed is:

1. A method comprising the following steps:
   (a) contacting a topographically structured stamp to an array of spots comprising lipid ink on a palette to force the lipid ink of each of the spots into recesses of the topographically structured stamp,
   (b) removing the palette from the topographically structured stamp so that at least some the lipid ink from each of the spots is retained in the recesses of the topographically structured stamp, and
   (c) printing the lipid ink in each of the recesses on a substrate as an array of stamped spots using the topographically structured stamp to thereby form a patterned substrate,
   wherein the recesses have one or more recess patterns,
   wherein each stamped spot of the array of stamped spots comprises lipid multilayer structure, and
   wherein the patterned array is based on the one or more recess patterns.

2. The method of claim 1, wherein at least some stamped spots of the array of stamped spots comprises a lipid and one or more drugs.

3. The method of claim 2, wherein at least two of the stamped spots of the array of stamped spots comprise the same drug in different concentrations.

4. The method of claim 2, wherein one or more stamped spots of the array of stamped spots comprise a lipid ink and two or more drugs.

5. The method of claim 4, wherein at least two of the stamped spots comprise the same two or more drugs and wherein the two or more drugs are present in different concentration ratios in the at least two or more stamped spots.

6. The method of claim 1, wherein one or more stamped spots of the array of stamped spots comprises a phospholipid.

7. The method of claim 1, wherein one or more stamped spots of the array of stamped spots comprises a mixture of two or more lipids.

8. The method of claim 1, wherein step (b) comprises moving the topographically structured stamp relative to the palette.

9. The method of claim 1, wherein step (b) comprises moving the palette relative to the topographically structured stamp.

10. The method of claim 1, wherein step (c) comprises moving the topographically structured stamp relative to the substrate.

11. The method of claim 1, wherein step (c) comprises moving the substrate relative to the topographically structured stamp.

12. The method of claim 1, wherein the recesses comprise one or more grooves.

13. The method of claim 1, wherein the lipid ink of one or more spots of the array of spots is a neat lipid ink.

14. The method of claim 1, wherein the stamped spots of the array of stamped spots are microstructures.

15. The method of claim 1, wherein the stamped spots of the array of stamped spots are nanostructures.

16. The method of claim 1, wherein the method comprises the following step:
   (d) depositing cells on the patterned substrate to thereby form a patterned substrate at least partially covered by the cells.

17. The method of claim 16, wherein step (d) comprises immersing at least the array of stamped spots of the patterned substrate in an aqueous solution containing the cells to thereby deposit the cells onto the patterned substrate.

18. The method of claim 1, wherein two or more spots of the array of spots comprise different lipid inks, and wherein two or more stamped spots of the array of stamped spots comprise different lipid inks.

* * * * *